(12) United States Patent
An

(10) Patent No.: US 9,078,640 B1
(45) Date of Patent: Jul. 14, 2015

(54) DISPOSABLE BIOPSY DEVICES AND METHODS OF OBTAINING TISSUE BIOPSY SAMPLES USING SAME

(71) Applicant: Byungseol An, Tuxedo, NY (US)

(72) Inventor: Byungseol An, Tuxedo, NY (US)

(*) Notice: Subject to any disclaimer, the term of this patent is extended or adjusted under 35 U.S.C. 154(b) by 0 days.

(21) Appl. No.: 14/590,214

(22) Filed: Jan. 6, 2015

Related U.S. Application Data

(63) Continuation of application No. 14/558,273, filed on Dec. 2, 2014.

(51) Int. Cl.
*A61B 10/00* (2006.01)
*A61B 10/02* (2006.01)

(52) U.S. Cl.
CPC ............. *A61B 10/0283* (2013.01); *A61B 10/02* (2013.01); *A61B 10/0275* (2013.01); *A61B 2010/009* (2013.01); *A61B 2010/0208* (2013.01)

(58) Field of Classification Search
CPC ............... A61B 10/02; A61B 10/0233; A61B 10/0275; A61B 10/0283; A61B 2010/0208
USPC .................................................. 600/562–567
See application file for complete search history.

(56) References Cited

U.S. PATENT DOCUMENTS

| 3,606,878 | A | * | 9/1971 | Kellogg, Jr. ................ 600/566 |
|---|---|---|---|---|
| 4,958,625 | A | | 9/1990 | Bates et al. |
| 5,368,045 | A | | 11/1994 | Clement et al. |
| 5,505,210 | A | | 4/1996 | Clement |
| 7,806,834 | B2 | * | 10/2010 | Beckman et al. ............ 600/566 |
| 8,343,073 | B2 | | 1/2013 | Miller |
| 8,398,566 | B2 | | 3/2013 | Goldenberg |
| 8,485,988 | B2 | | 7/2013 | Flatland et al. |
| 8,568,332 | B2 | | 10/2013 | Miller |
| 8,597,205 | B2 | | 12/2013 | Seiger et al. |
| 8,728,005 | B2 | | 5/2014 | McClellan |
| 8,740,810 | B2 | | 6/2014 | Sanbuichi |
| 8,740,811 | B2 | | 6/2014 | Fortems et al. |
| 8,744,552 | B2 | | 6/2014 | Akuzawa et al. |
| 8,764,679 | B2 | | 7/2014 | Miller et al. |

OTHER PUBLICATIONS

U.S. Appl. No. 14/558,273 (50 pages).

* cited by examiner

*Primary Examiner* — Brian Szmal
(74) *Attorney, Agent, or Firm* — Greenberg Traurig, LLP

(57) ABSTRACT

The described invention provides a disposable handheld biopsy device for taking biopsies, the biopsy device comprising a tissue cutting assembly which has features to control the tissue length that will be severed by the cutting assembly; and a vacuum assembly which has features to control the vacuum level. The disposable handheld biopsy device of the described invention is simple, lightweight, portable, and cost effective to manufacture and dispose of.

30 Claims, 19 Drawing Sheets

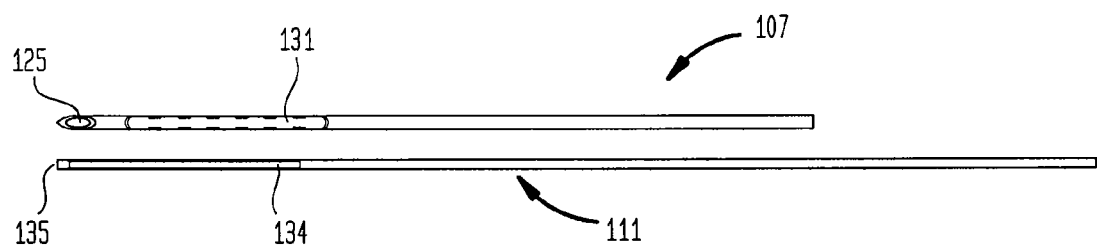
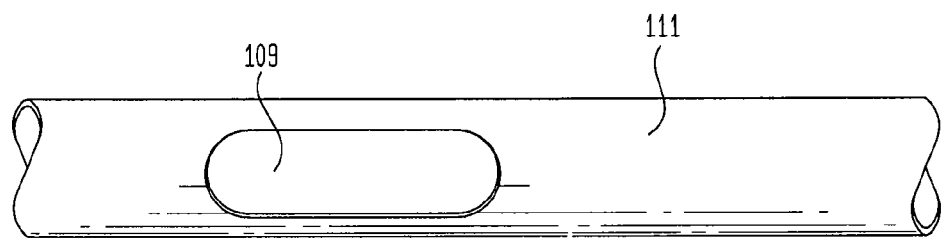
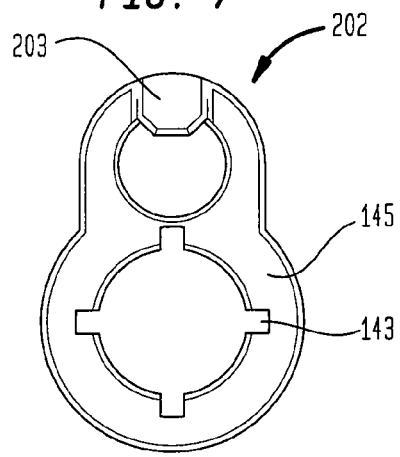

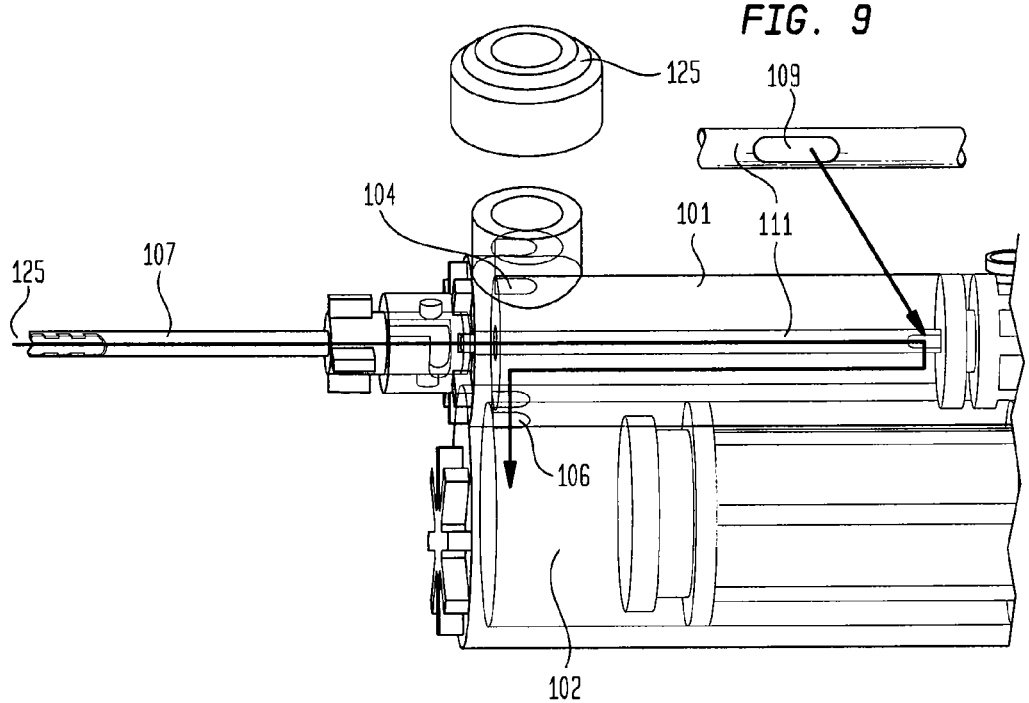
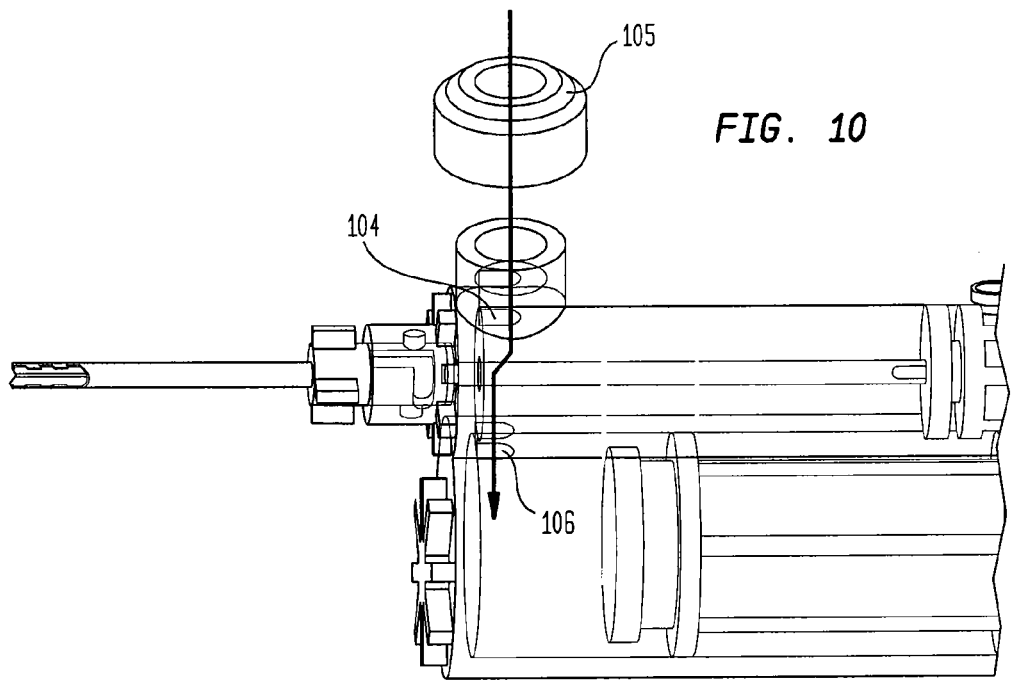

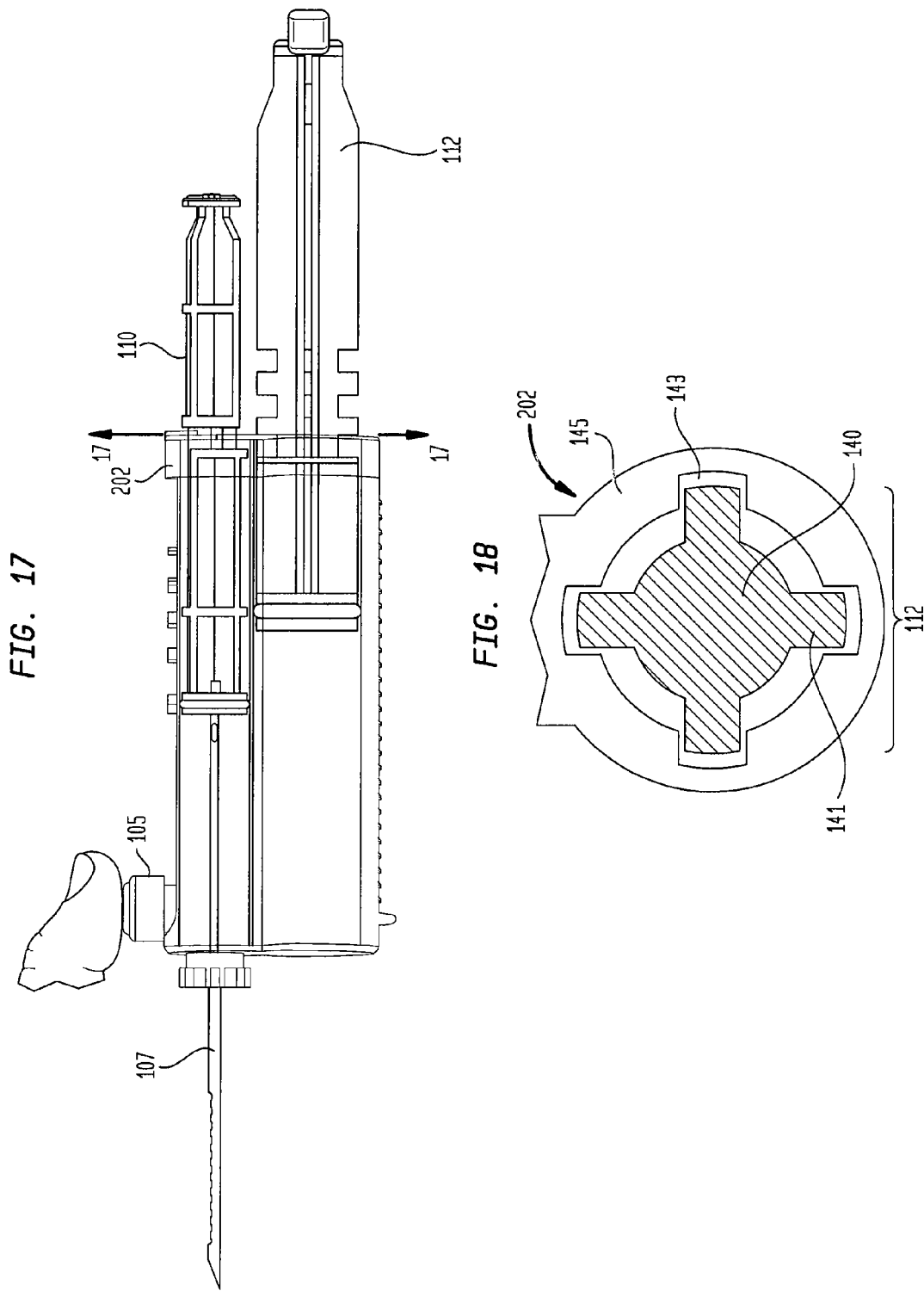

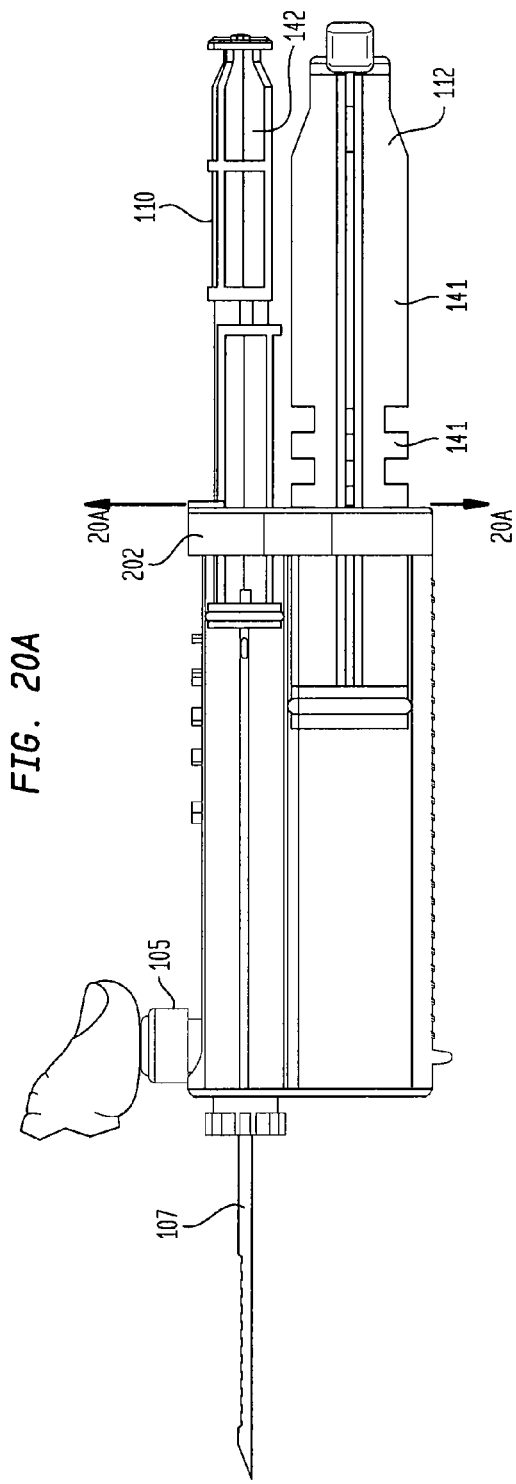
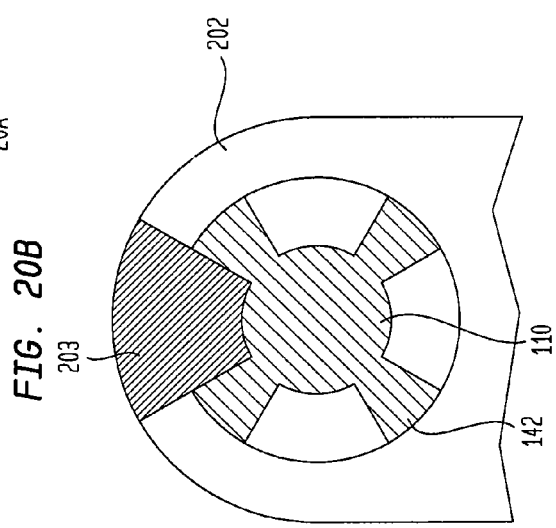
FIG. 20A
FIG. 20B

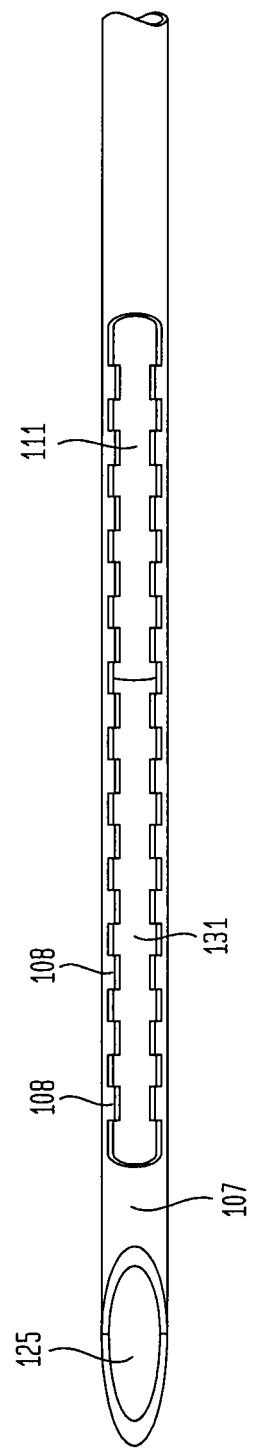

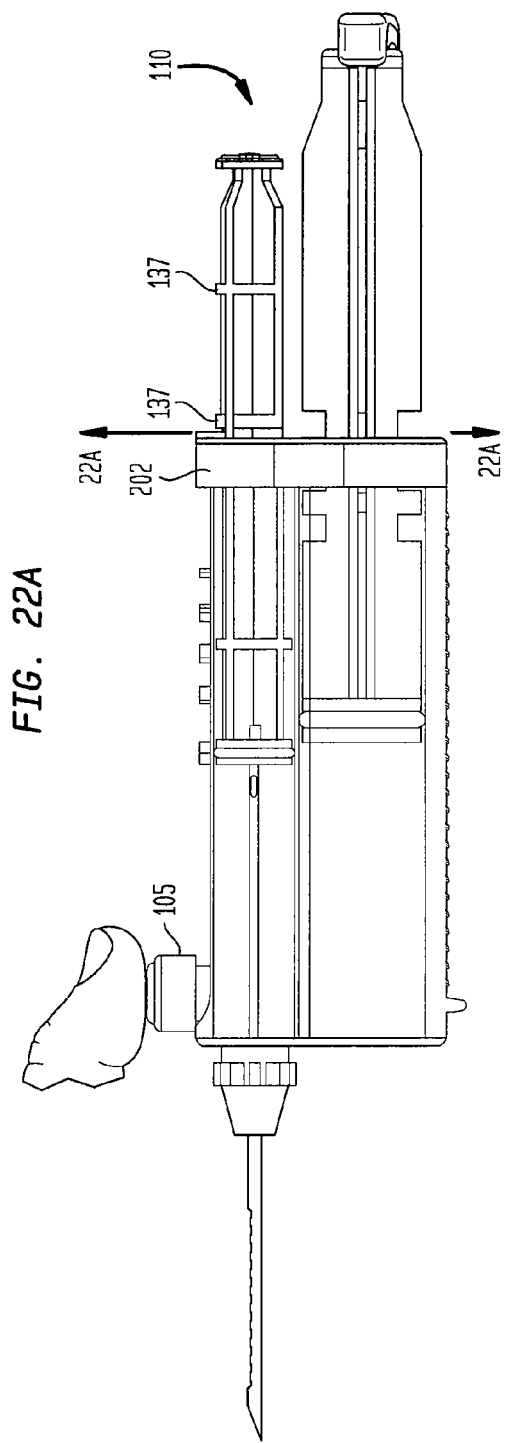
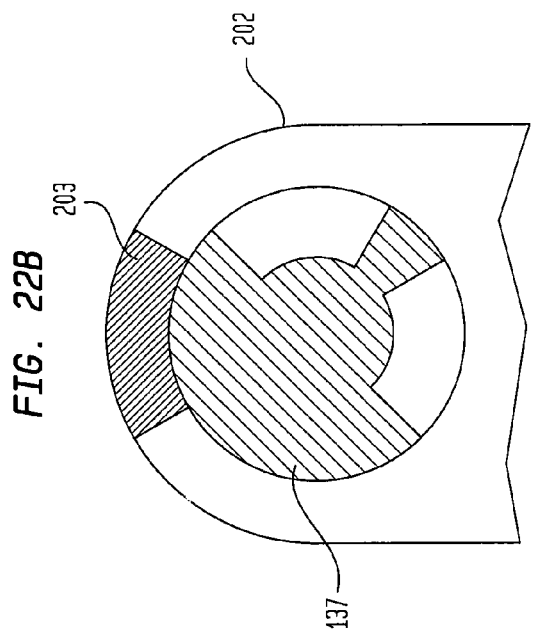
FIG. 22A
FIG. 22B

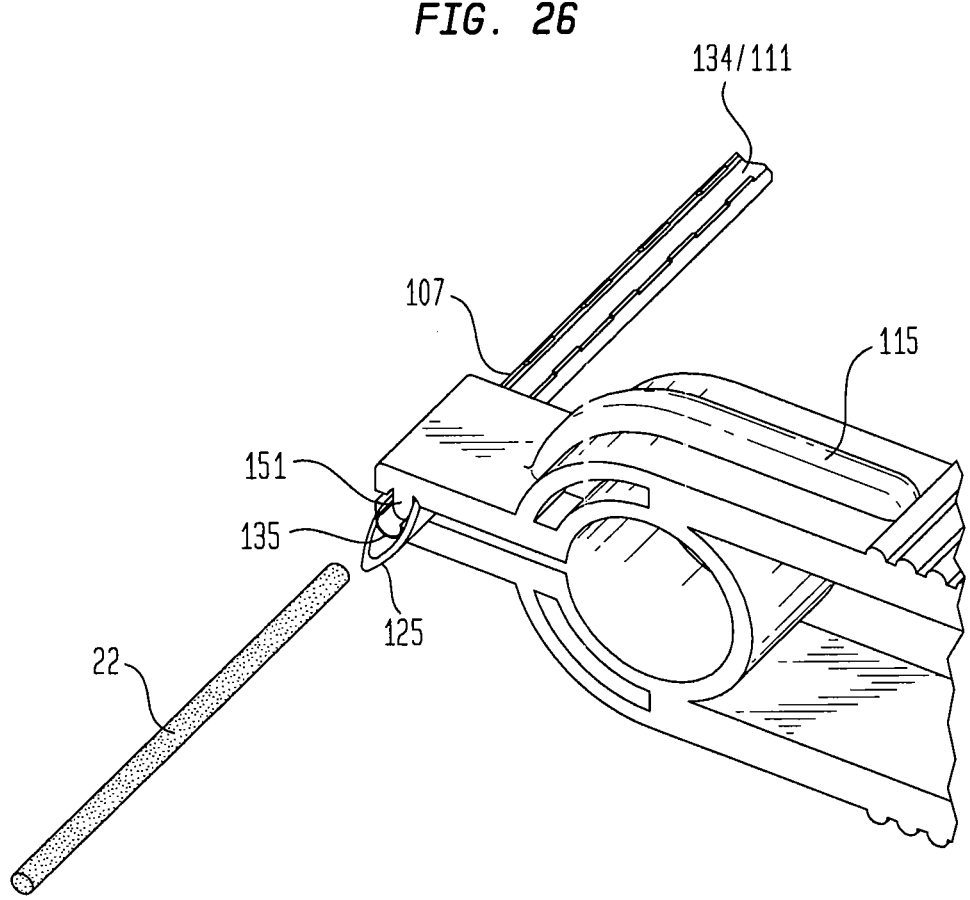

DISPOSABLE BIOPSY DEVICES AND METHODS OF OBTAINING TISSUE BIOPSY SAMPLES USING SAME

CROSS REFERENCE TO RELATED APPLICATION

This application is a continuation of U.S. application Ser. No. 14/558,273, filed Dec. 2, 2014, entitled "DISPOSABLE BIOPSY DEVICES AND METHODS OF OBTAINING TISSUE BIOPSY SAMPLES USING SAME," the content of which is incorporated by reference herein in its entirety.

FIELD OF THE INVENTION

The described invention generally relates to biopsy devices and methods of obtaining a tissue biopsy with the biopsy devices.

BACKGROUND OF THE INVENTION

A biopsy is a procedure to remove tissue from a patient for diagnostic examination that may involve taking a tissue sample and/or body fluid from a patient. Tests performed on the resulting tissue specimen can provide information for diagnosis of the patient's condition.

Biopsy samples have been obtained in a variety of ways in various medical procedures using a variety of devices. Biopsy devices may be used under stereotactic guidance, ultrasound guidance, magnetic resonance imaging (MRI) guidance, or otherwise. Exemplary biopsy devices include, without limitation, needle-based biopsy guns: for example, vacuum-assisted biopsy devices, fine needle aspiration biopsy devices (FNAB), and core needle biopsy devices; disposable and reusable biopsy needles; and biopsy forceps: general biopsy forceps and hot biopsy forceps, etc.

A biopsy may be obtained by an open or percutaneous technique. Open biopsy typically is an invasive surgical procedure which removes an entire mass or a part of the mass after an excision (denoting surgical removal of part or all of a structure)/incision (denoting surgical wound; a division of the soft parts usually made with a knife) is made. Percutaneous (denoting the passage of substances through unbroken skin and passage through the skin by needle puncture) biopsy is less invasive and usually is done with a needle-like instrument to collect a biopsy sample, for example, a fine needle aspiration (FNA) or a core biopsy. A FNA biopsy, which normally can be obtained for cytologic examination, generally includes individual cells or clusters of cells without preserving the histological architecture of the tissue cells. A core biopsy is a biopsy obtained for histologic examination in which a cylindrical sample of tissue is obtained using a hollow needle. The type of biopsy tools to be used depends on the circumstances. Typically, a core biopsy is used more frequently by the medical profession.

Methods and apparati for automated biopsy and collection of soft tissue are known. Many are cumbersome and not intended for disposable use. Methods that employ a vacuum chamber cannula to draw tissue into a receiving port where the vacuum chamber defines at least one, usually multiple, communicating holes between the chamber and the outer cannula, for example, are problematic in that these small holes often become clogged with blood and bodily fluids, such that the fluids occlude the holes and prevent the aspiration from drawing the tissue into the receiving port. This ultimately prevents a core from being obtained, a condition called a "dry tap." In addition, because many of the components of current biopsy devices are reusable, such as the driver portions, which control the outer and inner cutter needles, this can pose several disadvantages, for example, (1) the reusable portion must be cleaned and/or sterilized, which increases the time necessary to wrap up the procedure, which ultimately affects the cost of the procedure; (2) the required clean-up and/or sterilization of reusable parts increases the staffs' potential exposure to body tissues and fluids; (3) the reusable handle is heavy, large and cumbersome for handheld use.

A variety of biopsy needles and guns have been described and used for obtaining tissue specimens. In biopsy needles and guns that employ a manual vacuum generation mechanism, the mechanism often is complex, cumbersome, potentially expensive, and not disposable.

Most currently available biopsy devices involve complex mechanism, and thus are not intended to be disposable. Some of them rely on electric power to drive the motors for cutting and to establish a vacuum. Although some of the automated or manually actuated biopsy guns contain a disposable needle (stylus or cannula), replacing the disposable stylus or cannula can be troublesome and can pose a potential danger because this action exposes persons handling the needles to danger of infection. Also, in case the tissue touches other parts of the device, it could also expose the next patient or the medical professional to a potential health hazard.

In light of the foregoing disadvantages, a need exists for a disposable vacuum-assisted biopsy device which is simple, lightweight, portable, and cost effective to manufacture and dispose of.

SUMMARY

According to one aspect, the described invention provides a disposable biopsy device comprising: (A) a tissue cutting assembly comprising: an outer needle including a tissue receiving slot at a distal end of the outer needle; an elongated tube; an inner cutter needle including a tissue receiving port at a distal end of the inner cutter needle; a first plunger; and a first stopper; wherein (i) the outer needle is attached to a distal end of the tube; (ii) the inner cutter needle is attached to a distal end of the first plunger; (iii) the inner cutter needle and the first plunger are coaxially positioned within the tube and capable of rotating about and translating along the longitudinal axis of the tube; (iv) the inner cutter needle is coaxially positioned within the outer needle and capable of rotating about and translating along the longitudinal axis of the outer needle; (v) the first stopper is attached to or connected to a proximal end of the tube; and (B) a vacuum assembly comprising: an elongated cylinder; a second plunger; and a second stopper; wherein (i) the second plunger is coaxially disposed within the cylinder and capable of rotating about and translating along the longitudinal axis of the cylinder; and (ii) the second stopper is attached to or connected to a proximal end of the cylinder; wherein the vacuum assembly and the cutting assembly are two separate compartments in fluid communication through one or more air holes in between.

According to one embodiment of the disposable biopsy device, the tube has one or more air path holes on the bottom surface, the cylinder has one or more air path holes on the top surface and the inner cutter needle has one or more holes near its proximal end such that the vacuum generated by pulling the second plunger creates a low pressure region near the tissue receiving slot. According to another embodiment, the tube has an air release hole on a top surface of the tube for releasing the vacuum. According to another embodiment, the first plunger and the first stopper are configured to mate, thereby controlling a length of tissue to be severed from a tissue mass; and the second plunger and the second stopper are configured to mate, thereby controlling vacuum levels. According to another embodiment, the tube has a cutting length indicator which has numerical indicia corresponding to the length of tissue to be separated from the tissue mass. According to another embodiment, the first plunger comprises a plunger rod, one or more ridges, and one or more notches on the plunger rod, the first plunger together with the first stopper controlling the length of tissue to be severed. According to another embodiment, the first plunger comprises a plunger rod, a plurality of raised edges extending laterally therefrom, a plurality of ridges disposed at predetermined positions across adjacent raised edges, and a plurality of notches in front of or behind the ridges, the first plunger together with the first stopper controlling the length of tissue to be severed. According to another embodiment, the first plunger comprises a plunger rod, a plurality of raised edges extending laterally therefrom, and a plurality of ridges disposed at predetermined position across adjacent raised edges, wherein the first stopper is configured to engage the ridge on the first plunger, thereby stopping the plunger from moving forward and controlling the length of tissue. According to another embodiment, the first plunger has a plurality of notches thereon which allow the first plunger to be rotated, which disengages the first stopper and allows the first plunger to move further backward or forward. According to another embodiment, the second plunger comprises a plunger rod, and one or more ridges, and one or more notches on the plunger rod, the second plunger together with the second stopper controlling the vacuum levels. According to another embodiment, the second plunger and the second stopper work together to control the vacuum levels, the second plunger comprising a plunger rod, a plurality of raised edges extending laterally therefrom, and a plurality of ridges disposed at predetermined position across adjacent raised edges, which when engaged, the second stopper stops the forward or backward movement of the plunger, and a plurality of notches in front of or behind the ridges, which allow the plunger to freely rotate, so that the second stopper is disengaged and the plunger is allowed to move forward or backward. According to another embodiment, the second plunger comprises a plunger rod, a plurality of raised edges projecting laterally therefrom, and a plurality of notches breaking the raised edges, and the second stopper is configured to interlock the raised edge of the plunger and restrict the plunger from rotating freely, while the notches allow the plunger to rotate and disengage the second stopper. According to another embodiment, the sample receiving slot has saw teeth thereon along its lateral sides, which hold the tissue tightly prior to and at the time that the inner cutter needle advances to cut the prolapsed tissue from the tissue mass. According to another embodiment, the disposable biopsy device further comprises a sample collector, which grasps the severed tissue sample out of the inner cutter needle such that the tissue sample is securely handled. According to another embodiment, the disposable biopsy device further comprises a shell that closely encloses the tube and cylinder. According to another embodiment, the disposable biopsy device further comprises a silicone fitting on top of the air release hole that seals the air release hole when pressed and releases the vacuum inside the biopsy device when released. According to another embodiment, the distal end of the outer needle is open and sharp such that it is easy to insert into the tissue. According to another embodiment, the distal end of the inner cutter needle is open, beveled in shape, and contains a razor sharp edge that is effective to slice the tissue prolapsed into the tissue receiving slot and collect the severed tissue in its tissue receiving port.

According to another embodiment, the first and second stoppers are continued as one unit or are two separate units.

According to another aspect, the described invention provides a method for obtaining a tissue sample for biopsy examination using a disposable hand held biopsy device, the method comprising: (a) providing a disposable biopsy device, the device comprising: (i) a tissue cutting assembly comprising: an outer needle comprising a tissue receiving slot at a distal end of the outer needle and saw teeth along lateral sides of the tissue receiving slot; an elongated tube comprising an air release hole and a cutting length indicator on a top surface of the tube; an inner cutter needle comprising a tissue receiving port at a distal end of the inner cutter needle; a first plunger; a first stopper; a silicone fitting on top of the air release hole; and a tissue sample collector; wherein (i) the outer needle is attached to a distal end of the tube (ii) the inner cutter needle is attached to a distal end of the first plunger (iii) the inner cutter needle and the first plunger are coaxially positioned within the tube and capable of rotating about and translating along the longitudinal axis of the tube, (iv) the inner cutter needle is coaxially positioned within the outer needle and capable of rotating about and translating along the longitudinal axis of the outer needle, and (v) the first stopper is attached to or connected to a proximal end of the tube; and (ii) a vacuum assembly comprising: an elongated cylinder; a second plunger; and a second stopper; wherein (i) the second plunger is coaxially disposed within the cylinder and capable of rotating about and translating along the longitudinal axis of the cylinder; (ii) the second stopper is attached to or connected to a proximal end of the cylinder; wherein the vacuum assembly and the cutting assembly are two separate compartments in fluid communication through one or more air holes in between; and (b) placing the outer needle at a location of collecting sample tissue; (c) covering the air release hole; (d) withdrawing the second plunger, rotating the plunger, and locking the plunger in place; (e) pulling the first plunger backward such that its distal end is aligned with one of the numerical indicia on the cutting length indicator corresponding to a desired tissue length, exposing the tissue receiving slot on the outer needle so that the tissue prolapses into the sample receiving slot and is held tight by the vacuum and the saw teeth along the tissue receiving slot; (f) releasing the first plunger and the attached inner cutter needle, which are then propelled by a gradient pressure to advance into the tissue receiving slot and sever the tissue, which has prolapsed into the sample port, and stops when it hits the first stopper; (g) allowing the air flow into the biopsy device, releasing the vacuum; (h) pulling the biopsy device out from the body; and (i) once outside the body, (1) turning the first plunger clockwise until it stops; (2) pushing the first plunger all the way forwards; (3) grasping the severed tissue sample using the sample collector; and (4) pulling the severed tissue out from the distal end of the inner cutter needle.

According to one embodiment of the method, in step (a), the tube has one or more air path holes on the bottom surface, the cylinder has one or more air path holes on the top surface and the inner cutter needle has one or more holes near its proximal end, such that the vacuum generated by pulling the second plunger creates the low pressure region near the tissue receiving slot. According to another embodiment, in step (a), the first plunger and the first stopper are configured to mate thereby controlling the length of the tissue to be severed from the tissue mass; and the second plunger and the second stopper are configured to mate thereby controlling the vacuum levels. According to another embodiment, in step (a), the first plunger comprises a plunger rod, one or more ridges, and one or more notches on the plunger rod, the first plunger together with the first stopper controlling the length of tissue to be severed. According to another embodiment, in step (a), the first plunger comprises a plunger rod, a plurality of raised edges extending laterally therefrom, a plurality of ridges disposed at predetermined position across adjacent raised edges, and a plurality of notches in front of or behind the ridges, the first plunger together with the first stopper controlling the length of tissue to be severed. According to another embodiment, in step (a), the first plunger comprises a plunger rod, a plurality of raised edges extending laterally therefrom, a plurality of ridges disposed at a predetermined position across adjacent raised edges, wherein the first stopper is configured to engage the ridge on the first plunger thereby stopping the plunger from moving forward whereby controlling the tissue length and a plurality notches thereon, which allow the first plunger to be rotated, thereby dis-engaging the first stopper and allowing the first plunger to move further backward or forward.

According to another embodiment, in step (a), the second plunger comprises a plunger rod, one or more ridges, and one or more notches on the plunger rod, the second plunger together with the second stopper controlling the vacuum levels. According to another embodiment, in step (a), the second plunger and the second stopper work together to control the vacuum levels, the second plunger comprising a plunger rod, a plurality of raised edges extending laterally therefrom, and a plurality of ridges disposed at predetermined positions across adjacent raised edges, which when they engage the second stopper stops the forward or backward movement of the plunger, and a plurality of notches in front of or behind the ridges, which allow the plunger to freely rotate thereby disengaging the second stopper and allowing the plunger to move forward or backward. According to another embodiment, in step (a), the second plunger comprises a plunger rod, and a plurality of raised edges projecting laterally therefrom, wherein the second stopper is configured to interlock the raised edge of the plunger, restricting the plunger from rotating freely, and the plunger has a plurality of notches allowing the plunger to rotate and disengage the second stopper. According to another embodiment, in step (a), the disposable biopsy device further comprises a shell that closely encloses the tube and cylinder. According to another embodiment, in step (a), the distal end of the outer needle is open and sharp such that it is easy to insert into the tissue and the distal end of the inner cutter needle is open, beveled in shape, and contains a razor sharp edge, the distal end of the inner cutter needle slicing the tissue prolapsed into the tissue receiving slot and collecting the severed tissue in its tissue receiving port.

BRIEF DESCRIPTION OF THE DRAWINGS

FIG. 5 shows the dimensions of both the outer needle and inner cutting cannula.

FIG. 6 shows a close up view of the inner cutter needle having an air hole near the proximal end thereon.

FIG. 7 is a rear view of a mechanical stopper alone.

FIG. 9 is a close up distal end of the biopsy device showing the air passage when the silicone fitting on the air release hole is pressed and the primary suction plunger is pulled away from the distal end of the primary suction tube.

FIG. 10 is a close up distal end of the biopsy device showing the air passage when the silicone fitting on the air release hole is released.

FIG. 17 illustrates a side view of the biopsy device being at a position where the silicone fitting on the air release hole is pressed and the primary suction plunger is pulled all the way back to generate a vacuum.

FIG. 18 illustrates a partial cross sectional view of the biopsy device in FIG. 17 along the line 17-17 where when the plunger raised edges 141 are aligned with the notches of the stopper, the plunger freely moves in or out.

FIG. 19 B illustrates a partial cross sectional view of the biopsy device in FIG. 19A along the line 19A-19A where when the plunger raised edges 141 engage the board of the stopper, the plunger is locked in place.

FIG. 20 A is a side view of the biopsy device being at a position where the cutting plunger is pulled all the way back with its distal end aligned with the last mark of the length indicator.

FIG. 20 B illustrates a partial cross sectional view of the biopsy device in FIG. 20A along the line 20A-20A where when the grooves between the plunger raised edges 142 are aligned with the tab 203 of the stopper, the plunger freely moves in or out.

FIG. 21 is a close up view of the tissue receiving slot of the outer needle and the distal end of the inner cutter needle therein.

FIG. 22 A is a side view of the biopsy device after the cutting plunger is withdrawn toward the distal end of the cutting tube by the suction force, advances into the tissue mass and slices the prolapsed tissue from the tissue mass.

FIG. 22 B illustrates a partial cross sectional view of the biopsy device in FIG. 22A along the line 22A-22A where when the ridge 137 of the plunger is blocked by the tab 203 of the stopper, the plunger is locked in place.

FIG. 26 illustrates that the collected sample tissue falls off by gravity when the inner cutter needle is pulled backward.

DETAILED DESCRIPTION OF THE INVENTION

Figure 1:
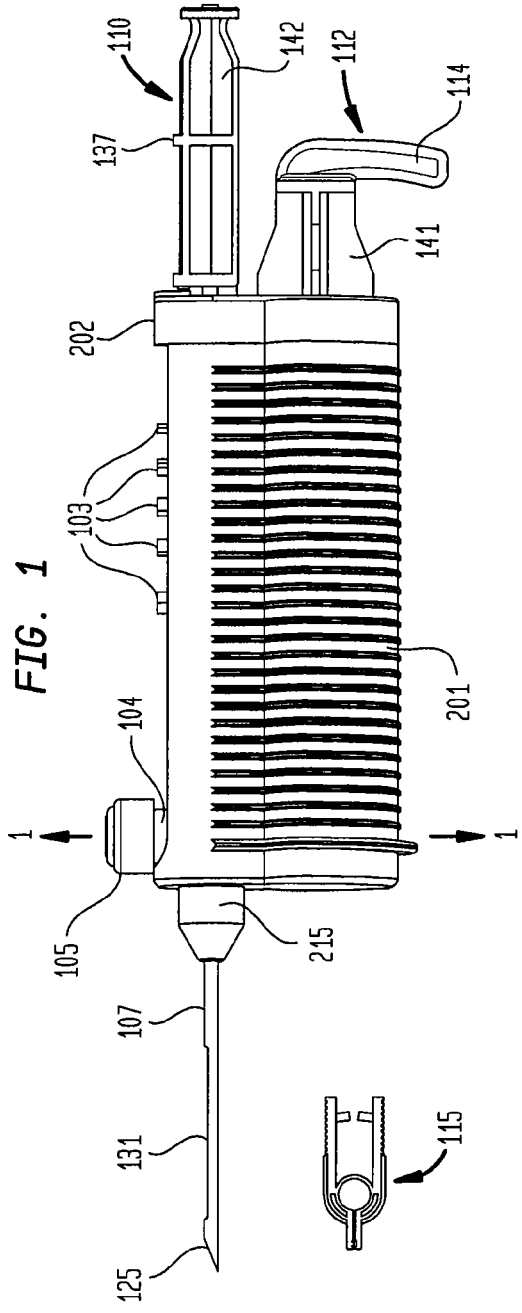
FIG. 1 is a side view of a biopsy device of the described invention including a cutting assembly on the top and a primary suction assembly on the bottom as well as a sample collector.

According to one aspect, the described invention provides a disposable biopsy device for obtaining a biopsy, the disposable biopsy device comprising a tissue cutting assembly, which has features to control the tissue length that will be severed by the cutting assembly. According to one embodiment, the tissue cutting assembly comprises a thin, elongated outer needle, a thin, elongated inner cutter needle, an elongated tube, and a first plunger. The outer needle is attached to the distal end of the elongated tube; the inner cutter needle is attached to the distal end of the first plunger (i.e. the cutting plunger), both of which are coaxially positioned within the tube and capable of rotating about and translating along the longitudinal axis of the tube. According to one embodiment, the inner cutter needle is coaxially positioned within the outer needle and capable of rotating about and translating along the longitudinal axis of the outer needle. According to one embodiment, the elongated tube has a cutting length indicator, which has numerical indicia to indicate the length of the prolapsed tissue to be separated from the tissue mass. According to one embodiment, the cutting plunger has a plunger rod, notches and ridges on the plunger rod, which engage the stopper to control the length of the tissue to be severed as desired. According to one embodiment, the elongated tube has an air release hole on a top surface of the tube and at least one air path hole on a bottom surface of the tube. According to one embodiment, the inner cutter needle has at least one hole near its proximal end.

The disposable biopsy device further comprises a vacuum assembly, which has features to control a vacuum level. According to one embodiment, the vacuum assembly comprises an elongated cylinder and a second plunger (i.e. the suction plunger) which is coaxially disposed within the cylinder and is movable around and along the longitudinal axis of the cylinder. According to one embodiment, the plunger has a plunger rod, ridges, and notches on the plunger rod, which engage with the stopper attached to the proximal end of the cylinder to control the vacuum level to be generated.

According to one embodiment, the vacuum assembly is in fluid communication with the cutting assembly through one or more air hole(s) between them. According to one embodiment, the vacuum assembly and the cutting assembly are two separate compartments, which are only connected through the air hole(s) in between. According to one embodiment, the vacuum assembly generates a vacuum based on the linear movement of a piston relative to a cylinder.

According to one embodiment, the cylinder has an air hole on a top surface of the cylinder which together with the air hole on the bottom surface of the tube forms an air path hole. The air hole in the inner cutter together with the air path hole allow the air to diffuse from the outer needle through the air hole in the inner cutter and through the air path hole between the tube and the cylinder to the cylinder when the suction plunger is pulled, thereby creating a low pressure region near the sample receiving slot in the outer needle. The suction force generated by the vacuum assembly pulls and traps the prolapsed tissue into a tissue sample receiving slot and holds the tissue tightly prior to and during cutting. The pressure gradient between the low pressure region and the outside ambient pressure propels the cutting plunger toward the low pressure area until it hits the stop position of the stopper, which is connected to the proximal end of the tube. Together with the cutting plunger, the attached inner cutter needle is propelled toward the tissue receiving slot and separates the prolapsed tissue from the tissue mass. According to another embodiment, the tissue sample receiving slot has saw teeth along its two lateral sides, which also hold the tissue tightly prior to and at the time that the inner cutter needle is advanced to separate the tissue from the tissue mass.

According to one embodiment, the biopsy device further comprises a sample collector which grasps the severed tissue sample out of the inner cutter needle such that the tissue sample is securely handled.

According to one embodiment, both the outer needle and inner cutter needle are formed of a surgical grade metal. According to one embodiment, the outer needle and inner cutter needle are formed of stainless steel. According to another embodiment, the outer needle and inner cutter needle are made of titanium or other materials. According to another embodiment, the outer needle and inner cutter needle are made of non-metallic material of appropriate strength and stiffness.

According to one embodiment, the mechanical stoppers for the suction plunger and cutting plunger are connected as one unit. According to another embodiment, the two mechanical stoppers are separate structures.

According to another aspect, the described invention also provides a method of obtaining a biopsy comprising: (1) providing a disposable biopsy device, the biopsy device including a tissue cutting assembly comprising means for controlling the length of tissue that will be severed by the cutting assembly; and a vacuum assembly comprising means for controlling how much vacuum is to be generated.

According to one embodiment, the tissue cutting assembly in step (1) comprises a thin, elongated outer needle, a thin, elongated inner cutter needle, an elongated tube, and a first plunger. The outer needle is attached to the distal end of the elongated tube; the inner cutter needle is attached to the distal end of the first plunger (i.e. the cutting plunger) both of which are coaxially positioned within the tube and capable of rotating about and translating along the longitudinal axis of the tube. According to one embodiment, the inner cutter needle is coaxially positioned within the outer needle and capable of rotating about and translating along the longitudinal axis of the outer needle. According to one embodiment, the elongated tube has a cutting length indicator, which has numerical indicia to indicate the length of the prolapsed tissue to be separated from the tissue mass. According to one embodiment, the cutting plunger has a plunger rod, notches and ridges on the plunger rod, which engage the stopper to control the length of the tissue to be severed as desired. According to one embodiment, the elongated tube has an air release hole on the top surface and at least one air path hole on the bottom surface. According to one embodiment, the inner cutter needle has at least one hole near its proximal end.

According to one embodiment, the vacuum assembly of step (1) of the method comprises an elongated cylinder and a second plunger (i.e. the suction plunger) which is coaxially disposed within the cylinder and is movable around and along the longitudinal axis of the cylinder. According to one embodiment, the plunger has a plunger rod, ridges and notches on the plunger rod, which engage with the stopper attached to the proximal end of the cylinder to control vacuum level to be generated.

According to one embodiment, the vacuum assembly of step (1) of the method is in fluid communication with the cutting assembly through one or more air hole(s). According to one embodiment, the vacuum assembly and the cutting assembly of step (1) of the method are two separate compartments, which are only connected through the air hole(s) in between. According to one embodiment, the vacuum assembly of step (1) of the method generates a vacuum based on the linear movement of a piston relative to a cylinder.

According to one embodiment, the cylinder of step (1) of the method has an air hole on the top surface which together with the air hole on the bottom surface of the tube forms an air path hole. The air hole in the inner cutter together with the air path hole allow the air to diffuse from the outer needle path through the air hole in the inner cutter and through the air path hole between the tube and the cylinder to the cylinder when the suction plunger is pulled, thereby creating a low pressure region near the sample receiving slot in the outer needle. The suction force generated by the vacuum assembly pulls and traps the prolapsed tissue into the sample receiving slot and holds the tissue tightly prior to and during cutting. The pressure gradient between the low pressure region and the outside ambient pressure propels the cutting plunger toward the low pressure area until it hits the stop position of the stopper, which is connected to the proximal end of the tube. Together with the cutting plunger, the attached inner cutter is propelled toward the tissue receiving slot and separates the prolapsed tissue from the tissue mass. According to another embodiment, the sample receiving slot has saw teeth along its two lateral sides, which also hold the tissue tight prior to and at the time that the inner cutter is advanced to separate the tissue from the tissue mass.

According to one embodiment, the biopsy device of step (1) of the method further comprises a sample collector which grasps the severed tissue sample out of the inner cutter such that the tissue sample is securely handled.

In step (1) of the method, according to one embodiment, both the outer needle and inner cutter needle are formed of a surgical grade metal. According to one embodiment, the outer needle and inner cutter needle are formed of stainless steel. According to another embodiment, the outer needle and inner cutter needle may be made of titanium or other materials. According to another embodiment, the outer needle and inner cutter may be made of non-metallic material of appropriate strength and stiffness.

According to one embodiment, the mechanical stoppers of step (1) of the method for the suction plunger and cutting plunger are connected as one unit. According to another embodiment, the two mechanical stoppers are separate structures.

The method further comprises the steps (2) placing the outer needle at a location for collecting sample tissue in a patient's body; (3) covering the air release hole (e.g., with a thumb or a finger); (4) pulling out the suction plunger, turning (or rotating) the plunger and locking the plunger in place; (5) pulling the cutting plunger backward to generate a vacuum such that its distal end is aligned with one or more numerical indicia on the cutting length indicator that corresponds to a desired tissue length, thereby exposing the tissue receiving slot on the outer needle, where the tissue will prolapse into and be held tight by the suction force and the saw teeth; (6) releasing the cutting plunger, which, together with the inner cutter needle is propelled toward a low pressure region by a pressure gradient between the low pressure region and ambient pressure until it finally hits the first stopper and stops; the inner cutter advancing into the tissue receiving slot and severing the tissue which has prolapsed into the tissue receiving slot; (7) removing the means for covering the air release hole to allow air flow into the biopsy device and de-vacuum; (8) removing the biopsy device from the patient's body; (9) outside the body, turning the cutting plunger until it stops; (10) outside the body, pushing the first plunger all the way forwards; (11) and outside the body, grasping the severed tissue sample using the tissue collector, and pulling the severed tissue out from the sample receiving port of the inner cutter needle.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials have been described. All publications mentioned herein are incorporated herein by reference to disclose and described the methods and/or materials in connection with which the publications are cited.

It must be noted that as used herein and in the appended claims, the singular forms "a", "and", and "the" include plural references unless the context clearly dictates otherwise.

The publications discussed herein are provided solely for their disclosure prior to the filing date of the present application and each is incorporated by reference in its entirety. Nothing herein is to be construed as an admission that the present invention is not entitled to antedate such publication by virtue of prior invention. Further, the dates of publication provided may be different from the actual publication dates which may need to be independently confirmed.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Although the exemplified biopsy device is manually powered, the same inventive principles can apply to an automatic tissue biopsy device. Likewise, although the exemplified biopsy device is handheld, the same inventive principles can apply to a tissue biopsy device that is mounted on a support fixture.

Figure 2:
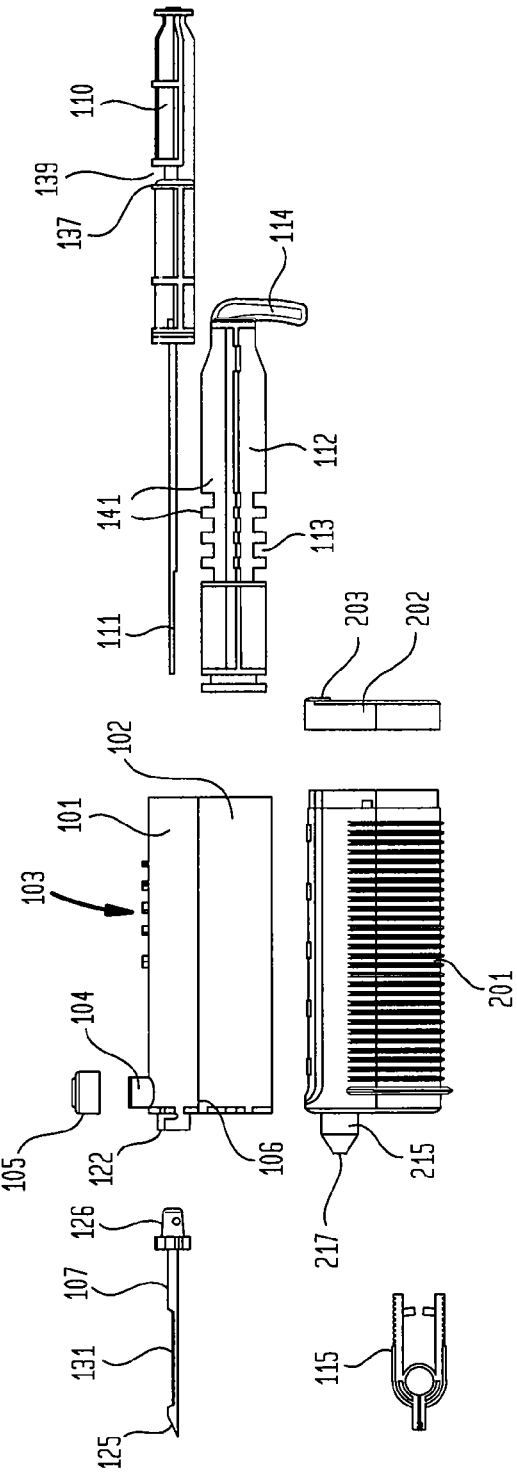
FIG. 2 is an exploded view of the biopsy device of the described invention shown in FIG. 1.

FIGS. 1 and 2 show an exemplary tissue biopsy device 10 that is manually powered for both tissue sample cutting and vacuum generation. The tissue biopsy device 10 of the described invention is configured as a handheld device. However, the same inventive principles can be employed in a tissue biopsy device that is mounted on a support fixture. The biopsy device 10 comprises a cutting assembly for taking tissue samples and a vacuum assembly for generating a vacuum.

Figure 3:
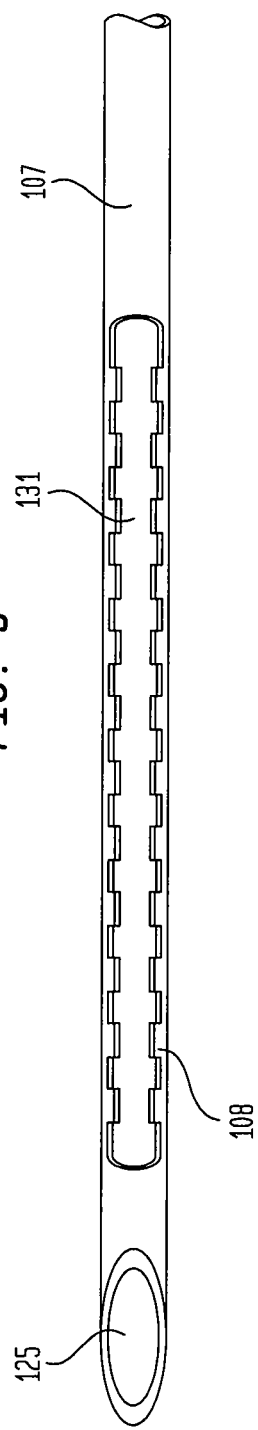
FIG. 3 is a close up view of an outer needle having saw teeth along the tissue receiving slot near the open distal end thereon.

The cutting assembly includes a thin, long outer needle 107 attached to the distal end of the cutting tube 101. The outer needle 107 defines an outer lumen (FIG. 3) that is hollow along the entire length of the outer needle to provide for aspiration of the biopsy sample. The cutting assembly further includes an inner cutter needle 111 that fits concentrically (or coaxially) within the outer needle 107. The thin elongated inner cutter needle 111 is attached to the distal end of a cutting plunger 110. The inner cutter needle 111 and cutting plunger 110 are configured to be able to move inside, about, and along the longitudinal axis (or length) of the close-fitting cutting tube 101. The inner cutter needle 111 is configured to be able to extend beyond the cutting tube 101 into the close-fitting hollow outer needle 107, and moves about and along the longitudinal axis of the outer needle 107. When the plunger 110 is pushed all the way in, the distal end of the inner cutter needle 111 can extend beyond the open distal end 125 of the outer needle 107.

The outer needle 107 has an open distant end 125 which is configured to penetrate tissue like a standard needle tip, a proximal end 126 attached to the distal end 121 of the cutting knife tube 101, and a tissue receiving slot 131 located proximal to the open distal end 125, which communicates with the outer lumen 127. The needle tip 125 is comparable to standard syringe needle tip, typically, for example, a standard bevel shape or short bevel shape.

Figure 4:
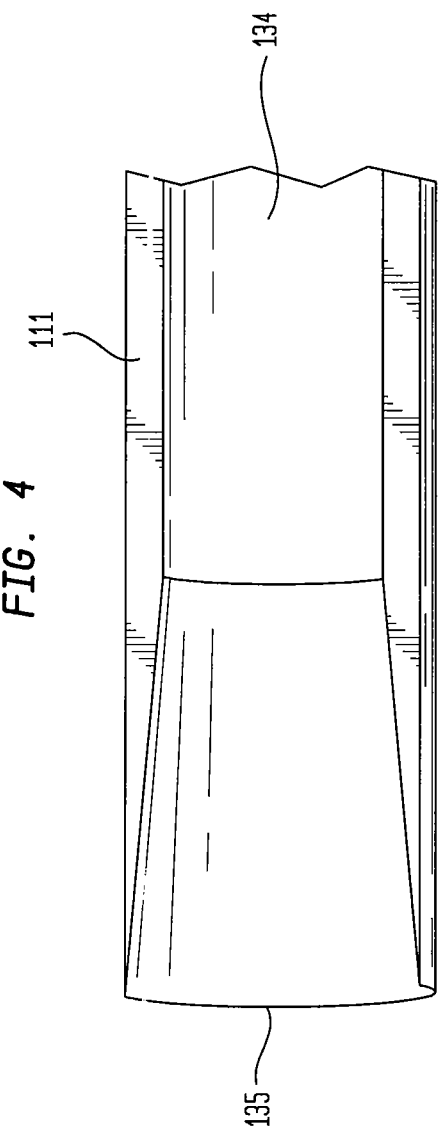
FIG. 4 is a close up view of an inner cutter needle having a tissue receiving port terminated by an inwardly beveled razor sharp edge at a distal end thereon.

The inner cutter needle 111 defines an inner lumen that is hollow along the entire length of the inner cutter needle to provide for aspiration of the biopsy sample. The inner cutter needle has a tissue receiving port 134, which communicates with the inner lumen and terminates in a razor sharp cutting edge 135, which is inwardly beveled at the distal end. The inwardly beveled edge helps eliminate the risk of catching the inwardly beveled edge on the tissue-sampling slot 131 of the outer needle. In addition, the beveled edge helps to avoid pinching the biopsy material between the inner and outer needles during a cutting stroke (FIG. 4). The inner cutter 111 further has an air hole 109 located near the proximal end of the needle 111 (FIG. 6), which is a part of the suction air pathway and will be further discussed later. The suction air pathway provides a mechanism for trapping and holding the tissue in place to enhance the cutting efficiency.

Moreover, the outer needle 107 further includes saw teeth cutouts 108 (FIG. 3) along two lateral sides of the tissue receiving slot 131 for holding the tissue in place to enhance the cutting efficiency.

According to one embodiment, both the outer needle 107 and the inner cutter needle 111 are formed of a surgical grade metal. For example, the two needles are formed of stainless steel.

The extent of the translation of the inner cutter needle 111 within the outer needle 107 is controlled by the configuration of the cutting plunger 110 relative to the cutting plunger stopper 203. The cutting plunger 110 is configured such that it can be pulled out to several pre-determined distances relative to the cutting tube 101 corresponding to the desired tissue lengths. A variety of configurations are possible to control the translation of the inner cutter needle 111 within the outer needle 107.

Figure 14:
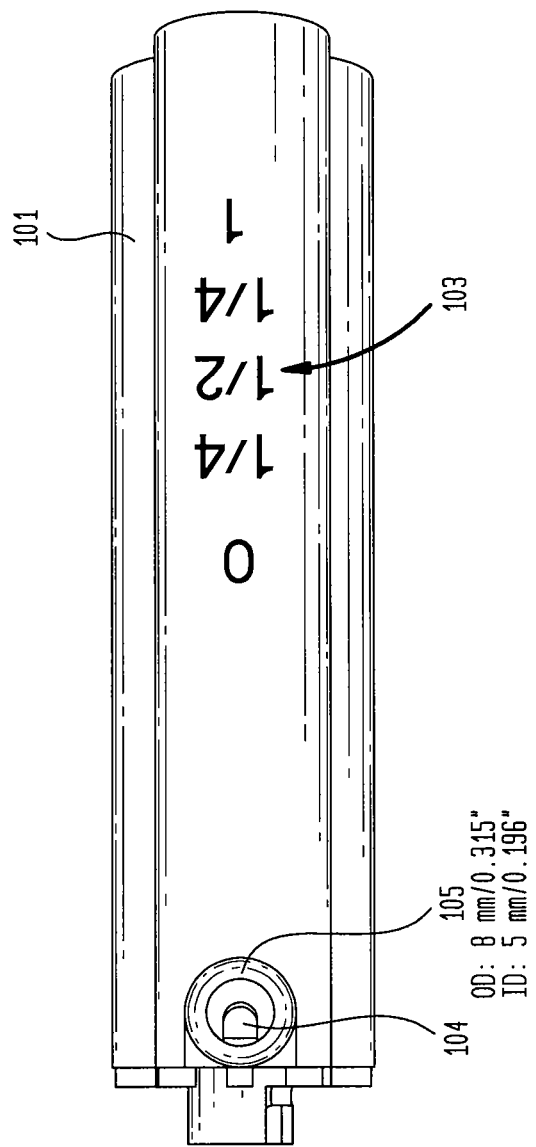
FIG. 14 shows the cutting length indicator and the diameter of a silicone fitting, which seals the air release hole on the top of cutting tube.

One example is illustrated in FIGS. 1 and 2. According to one embodiment, the cutting plunger 110 comprises a plurality of ridges 137 disposed at pre-determined locations (FIGS. 1 and 2). Once one of the plunger's ridges 137 encounters the tab 203 of the mechanical stopper 202 (FIG. 7), the plunger is locked in place (meaning forward movement is prevented). The cutting plunger 110 also has a plurality of notches 139 in front of or behind the ridges 137, which allows the cutting plunger 110 to rotate and bypass the ridges 137 so that the plunger 110 can make further movement. The biopsy device 10 further has a cutting length indicator 103 (as shown in FIG. 14) to enable a user to set a desired length of biopsy tissue. For example, if a tissue of one inch is desired, a user will align the distal end of the cutting plunger with the numerical indicia marked "one inch" on the indicator 103. This mechanism ensures that an accurate tissue length is sampled for further examination.

Similarly, the vacuum level is regulated by the configuration of the primary suction plunger 112 relative to the configuration of the stopper 202. A variety of configurations are possible. According to one embodiment as shown in FIGS. 1 and 2, the suction plunger 112 has a plurality of raised edges 141 along the plunger rod 140, and notches 113 breaking the raised edges (FIG. 2). The stopper 202 has notches 143 (FIG. 7) compatible with the raised edges on the plunger 112 such that the plunger can move backward and forward relative to the suction tube 102 as long as the raised edges 141 of the plunger engage the notches 143 of the stopper.

Once the plunger 112 is pushed/pulled to a desired position for a desired level of vacuum, the user turns/rotates the plunger such that the raised edges 141 of the plunger engages to another part 145 of the stopper, thereby locking the plunger 112 in place.

The primary suction tube 102 is closed at the distal end, and open at the primary end for receiving the primary suction plunger 112. The outer needle 107 is attached to the distal end of the cutting tube 101. The distal end of the cutting tube 101 may have a nozzle 122 for receiving the outer needle 107 and allowing the inner cutter needle to move in and out of the cutting tube. The suction plunger has a handle at the proximal end 114 to help manipulation.

Figure 8:
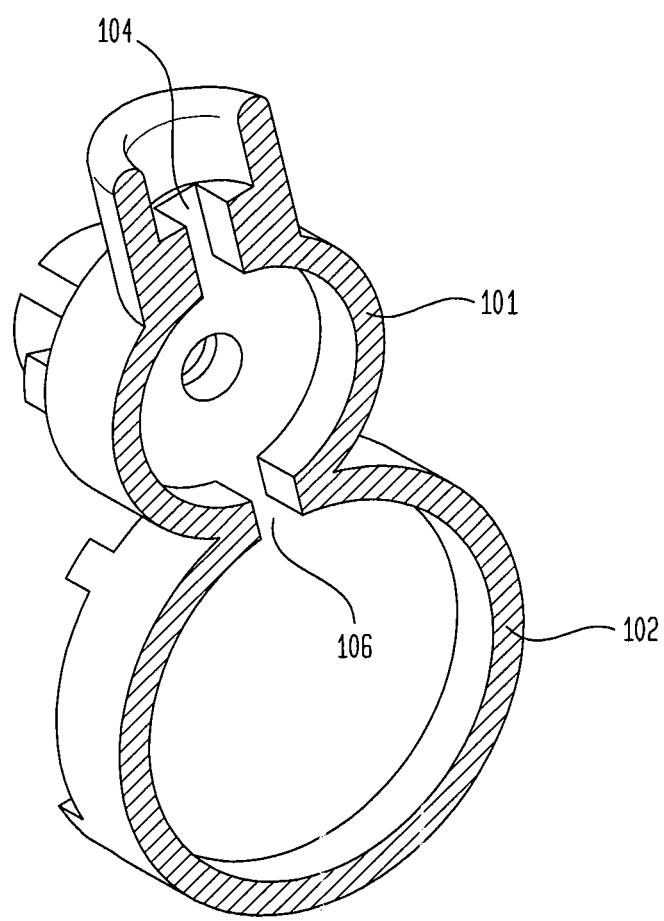
FIG. 8 is a cross sectional view of the biopsy device along line 1-1 in FIG. 1 showing an air path hole between the cutting needle tube and primary suction tube; and an air release hole on the top of the cutting needle tube.

The bottom surface of the cutting tube 101 is connected to the top surface of the primary suction tube 102, forming a shape with a cross sectional view of "8". Although their exteriors are connected, their interior compartments are substantially separate from each other. The only connection between the two interior compartments is an air path hole 106 located near the distal end in the wall between the cutting tube 101 and the primary suction tube 102. FIG. 8 is a cross sectional view of the biopsy device where the air path hole 106 is shown.

The tissue receiving port 134, the air hole 109 of the inner cutter needle 111, and the air path hole 106 together form a suction air pathway when the primary suction plunger 112 is pulled. FIG. 9 illustrates such a suction air pathway which is indicated as a thick solid line.

The air hole 109 at the proximal end on the inner cutter needle 111 and the air path hole 106 at the wall between the cutting tube 101 and the primary suction tube 102 provide an air pathway between the hollow interior of the outer needle and the hollow interior of the primary suction tube. The low pressure region created by the vacuum near the tissue receiving slot facilitates the prolapse (meaning sinking down or dropping) of the tissue sample into the immediately adjacent tissue sample slot.

The cutting tube 101 further has an air release hole 104 on the top near the distal end. The air release hole 104 and the air path hole 106 form an outlet for releasing the vacuum. FIG. 10 illustrates such a vacuum release pathway, which is indicated as a thick solid line.

The biopsy device can have a variety of dimensions. For example, the outer needle is about 50-150 mm in length and 1.27-2.41 mm in outer diameter (O.D.), which corresponds to a gauge 13-17 needle, and the sample receiving slot is about 5-25 mm in length. The inner cutter needle is about 80-180 mm long and 1.07-1.83 mm O.D., which corresponds to a gauge 15-19 needle, and the sample receiving port is about 32 mm long. The cutting plunger is about 90 mm long. The cutting tube is about 88 mm in length, 10-14 mm in inner diameter (I.D.) and 12.5-16.5 mm in O.D. The primary suction tube is about 80 mm long and 14-20 mm I.D. and 16.5-22.5 mm O.D. According to one embodiment, the cutting knife assembly further includes a silicone fitting 105 on top of the air release hole 104 to allow the air release hole to be closed by a finger or a thumb when necessary. The silicone fitting is of a size of about 6-8 mm I.D. and 8-10 mm O.D.

Figure 11:
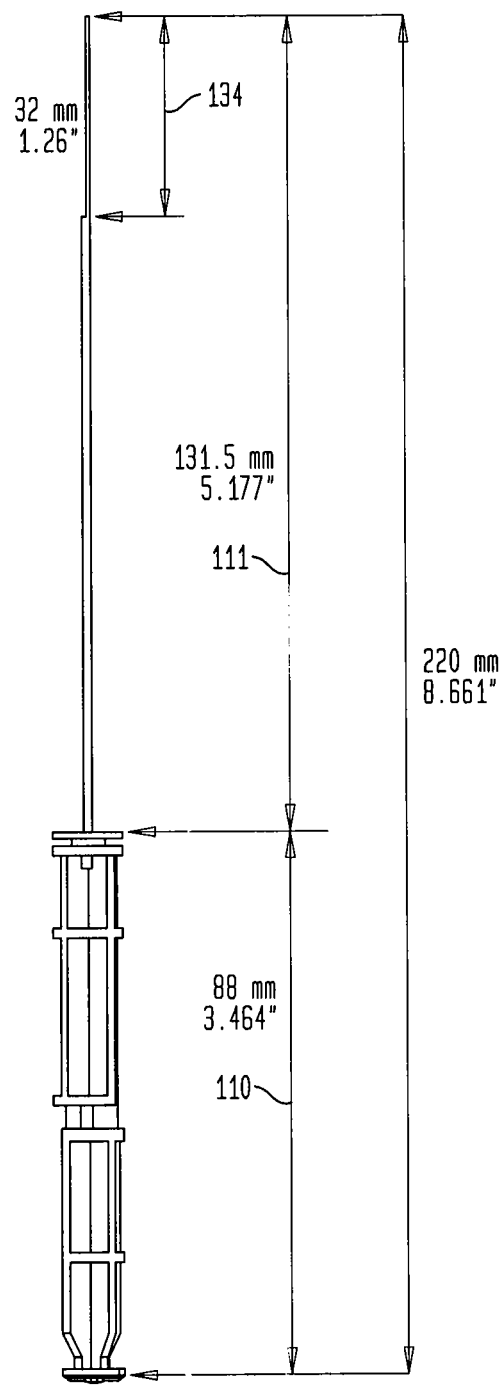
FIG. 11 shows the dimensions of the cutting plunger and the inner cutter needle attached thereto.
Figure 12:
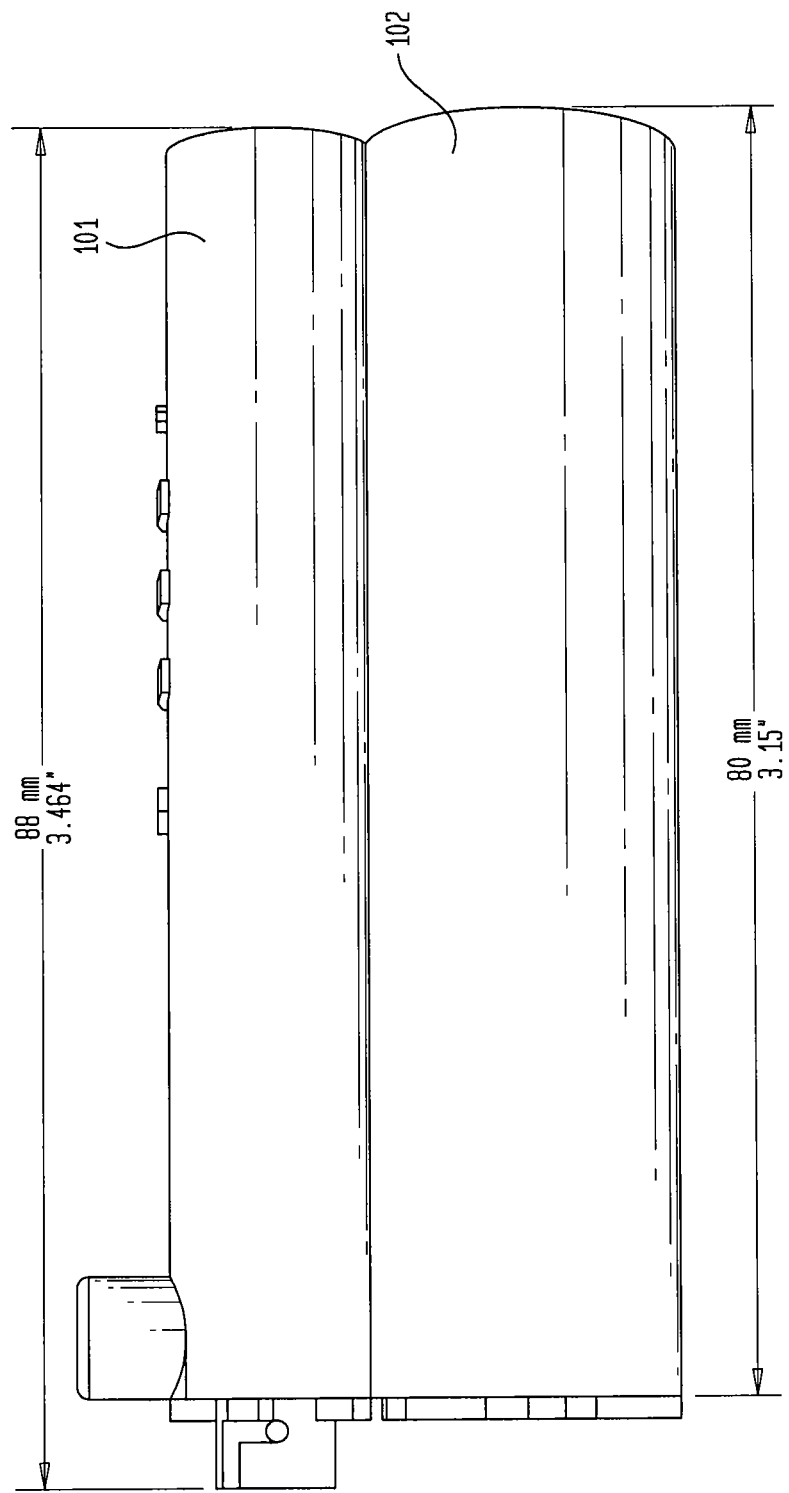
FIG. 12 shows the lengths of the cutting tube and the primary suction tube.
Figure 13:
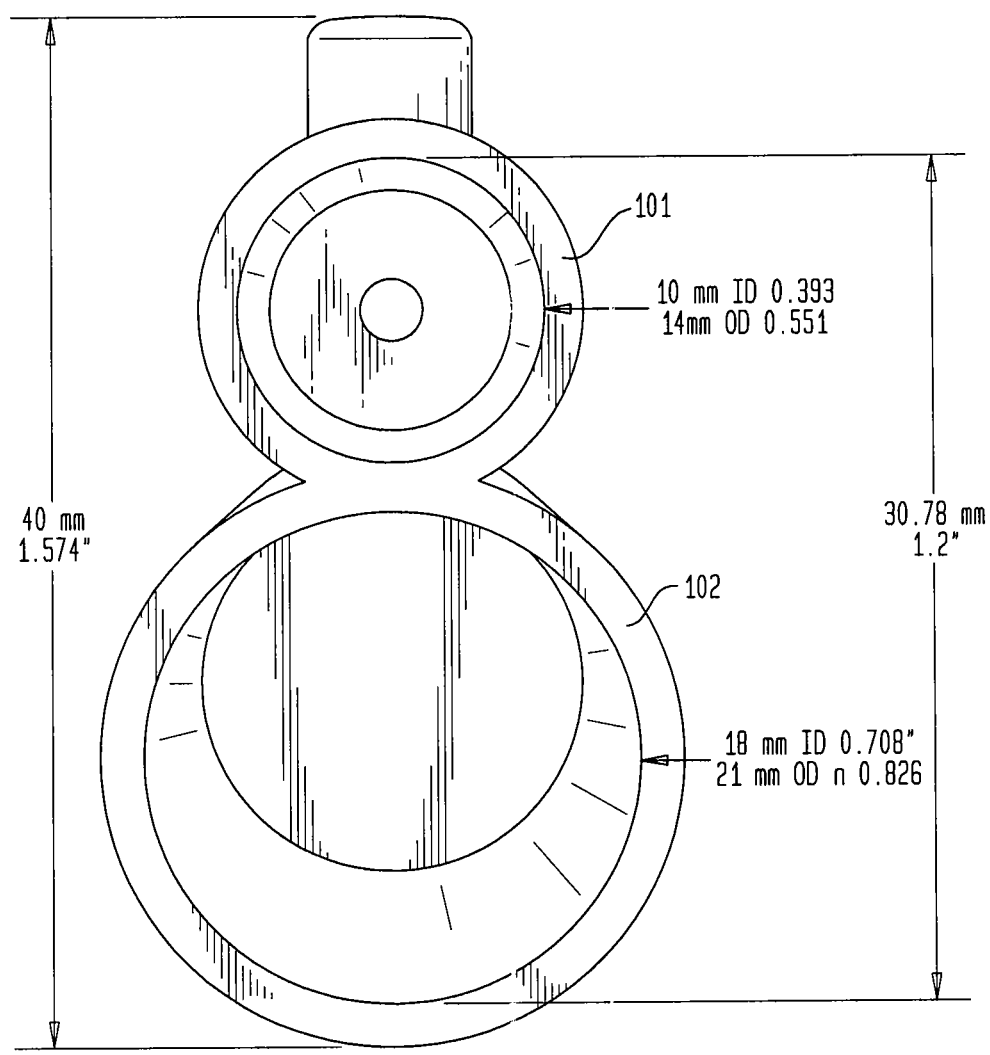
FIG. 13 shows the diameters of the cutting tube and the primary suction tube.

According to one particular device, the outer needle is about 100 mm in length and 1.83 mm in outer diameter (O.D.), which corresponds to a gauge 15 needle, and the sample receiving slot is about 25 mm in length. The inner cutter needle is about 137.5 mm long and 1.27 mm O.D., which corresponds to a gauge 18 needle, and the sample receiving port is about 32 mm long (FIG. 5 and FIG. 11). The cutting plunger is about 88 mm long (FIG. 11). The cutting tube is about 80 mm in length, 10 mm in inner diameter (I.D.) and 14 mm in O.D. The primary suction tube is about 80 mm long and 18 mm I.D. and 21 mm O.D. (FIGS. 12 and 13). The silicone fitting is of a size of about 5 mm I.D. and 8 mm O.D. (FIG. 11).

Both the cutting plunger and the primary suction plunger are tightly (closely) fit with the cutting tube and the primary suction cylinder, respectively. The distal end of both plungers can include, for example, silicone to ensure that the cutting and vacuum assemblies are air tight.

The cutting length indicator 103 has numerical indicia, for example, 0, ¼, ½, ¾, and 1 corresponding to 0, ¼, ½, ¾ and 1 inches. As shown in FIG. 14, according to one embodiment, the cutting length indicator 103 can be printed on the top surface of the cutting tube 101 to indicate the tissue length desired to be severed when the distal end of the plunger is aligned with that mark.

According to one embodiment, the biopsy device 10 further comprises a shell 201, which has an upper portion closely enclosing the cutting tube 101 and a lower portion closely enclosing the primary suction tube 102. The upper portion has a viewing window 211, which can be transparent or translucent, for viewing the tissue length indicator printed on the cutting tube 101. According to another embodiment, the window itself is a cutting length indicator showing the numerical indicia if the cutting length indicator is not printed on the cutting tube. The shell 201 further has a hole (not shown) open to the air release hole on the cutting knife tube 101. In the distal end of the upper portion, a protruding part 215 shaped to adapt to a nozzle 122 has an aperture 217 allowing the outer needle 107 to go through and inner cutter needle 111 to move in and out.

According to one embodiment, a stopper 202 is disposed at the proximal end of the cutting tube 101 and primary suction tube. According to another embodiment, the stopper 202 is disposed at (or attached to) the proximal end of a shell 201 as shown in FIGS. 1 and 2.

Figure 15:
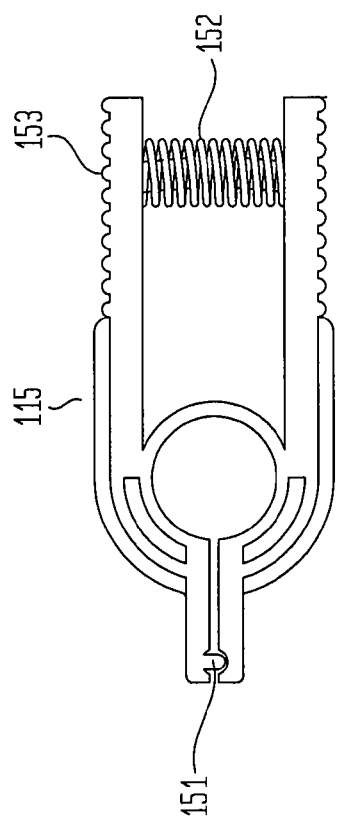
FIG. 15 shows a sample collector.

According to one embodiment, the biopsy device further comprises a sample collector 115 (FIG. 15). The sample collector has a clip 151 to grasp the tissue and the open space around the clip allows the clip to slide around the inner cutter's tissue receiving port 134 and move the tissue sample forward out of the port 134. In this way, the sample tissue can be kept intact and undamaged for further examination. The handle 153 is for the user to hold the sample collector 115.

Figure 16:
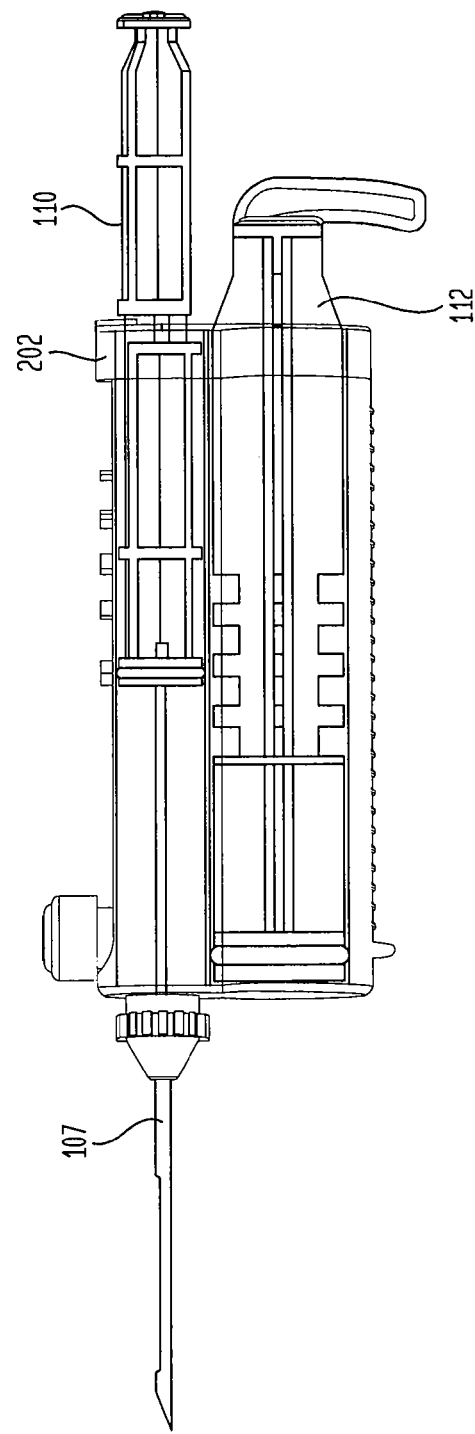
FIG. 16 shows the biopsy device at a ready to use position.

In operation, the user prepares the biopsy device in a ready to use position. Referring to FIG. 16 there is disclosed a ready to use biopsy device of the described invention, where the distal end of the cutting plunger 110 is aligned with the zero mark of the cutting length indicator 103 and the primary suction plunger 112 is fully pushed inside the suction tube 102.

The biopsy device 10 is handheld and the distal end 125 of the outer needle 107 is inserted into the precise location of the patient within the tissue 20 from which it is desired to obtain a tissue sample.

Figure 19A:
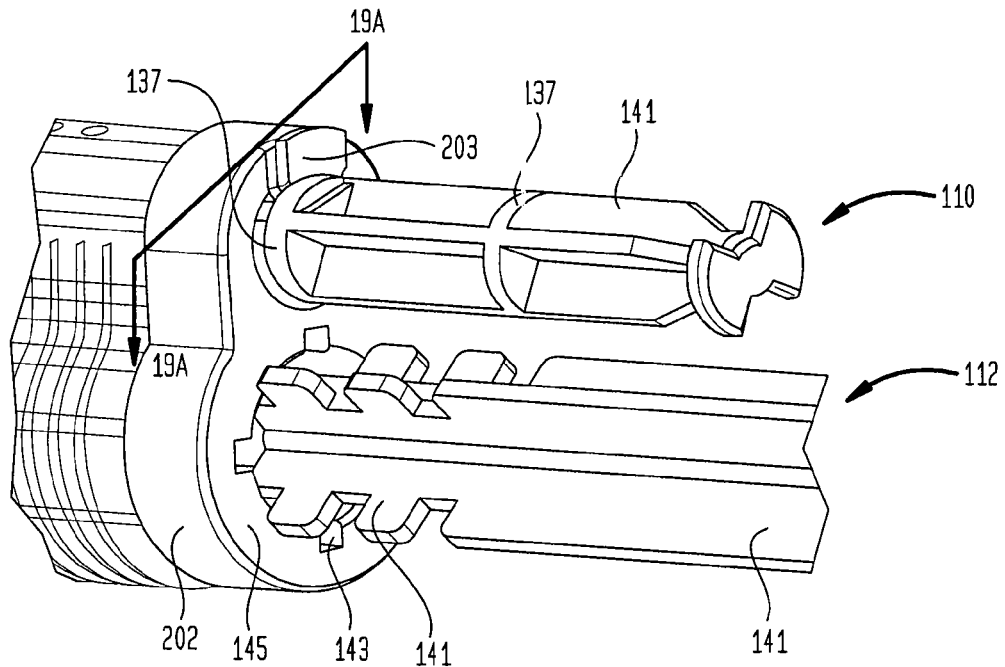
FIG. 19 A is an isometric view of the biopsy device showing that the raised edges of the plunger engage the board of the stopper thus locking the plunger in place after the plunger is turned.
Figure 19B:
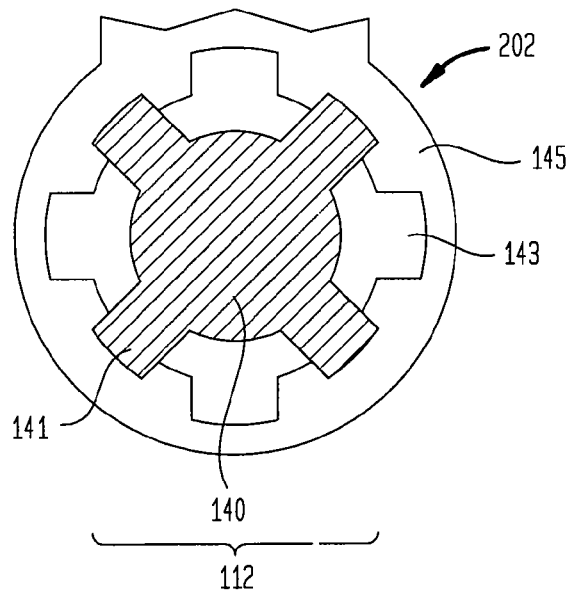

After the air release hole silicon fitting 105 is pressed (as demonstrated in FIG. 17), the primary suction plunger 112 is pulled towards the proximal end of the primary suction tube 102 to generate vacuum (FIG. 17). Then, the plunger is turned clockwise about 45 degrees to lock it in place as shown in FIG. 19 A. This action creates a vacuum in the biopsy device. FIGS. 18 and 19 B illustrate the locking mechanism. FIG. 18 is a cross sectional view of the biopsy device in FIG. 17 along the line 17-17, where when the plunger raised edges 141 are aligned with the notches 143 of the stopper 202, the plunger freely moves in or out. FIG. 19 A is an isometric view of the biopsy device showing the raised edges 141 of the plunger engage the board 145 of the stopper 202 after the plunger is turned, thus locking the plunger in place and securing the vacuum inside the tube. Thus, the user can manipulate the cutting plunger in the next step. If the user desires to move the suction plunger further distant, the user needs to rotate the plunger such that the interlocking can be disengaged. FIG. 19 B illustrates a cross sectional view of the biopsy device in FIG. 19 A along the line 19A-19A, where when the plunger raised edges 141 engage the board 145 of the stopper, the plunger is locked in place. The vacuum level generated within the biopsy device depends on how far the plunger is pulled away from the distal end of the suction tube. For example, the biopsy device shown in FIG. 2 provides four (4) vacuum levels.

According to another embodiment, the second plunger comprises a plunger rod, a plurality of raised edges extending laterally therefrom, and a plurality of ridges disposed at predetermined position across adjacent raised edges, and a plurality of notches in front of or behind the ridges, which together with the second stopper, control the vacuum levels.

The air hole 109 at the proximal end on the inner cutter needle and the air path hole 106 at the wall between the cutting tube 101 and the primary suction tube 102 provides an air passageway between the hollow interior of the outer needle and the hollow interior of the primary suction tube. The low pressure created by the suction in the region near the tissue receiving slot can facilitate the prolapse of the tissue immediately adjacent the tissue receiving slot into the tissue receiving slot.

The distal end of the cutting plunger 110 is then aligned to the one of the numerical indicia on the cutting length indicator 103 that shows the desired tissue length to be severed. FIG. 20 shows that the biopsy device 10 is in a position which is ready to cut sample tissue where the cutting plunger 110 is pulled with the distal end aligning with the "one inch" mark on the sample length indicator 103. As shown in FIG. 21, when the cutting plunger 110 is pulled, the distal end of the inner cutter needle 111 is pulled away from the distal end of the outer needle 107, thereby opening the tissue receiving slot 131. Due to the strong suction force created by the primary suction assembly, the tissue receiving slot 131 is filled with the solid and evenly distributed tissue sample. This prolapsed tissue sample will be tightly held during the process of biopsy (from beginning to end) by the suction force (vacuum) and by the saw teeth cut out 108.

FIG. 20 B illustrates a cross sectional view of the biopsy device in FIG. 20 A along the line 20 A-20 A where when the grooves between the plunger raised edges 142 are aligned with the tab 203 of the stopper, the plunger freely moves in or out.

After the cutting plunger 110 is released, the pressure gradient between the low pressure region and the outside ambient pressure propels the cutting plunger toward the low pressure area until it hits the stopping position 203 of the mechanic stopper 202. Together, the attached inner cutter 111 is propelled toward the tissue receiving slot and the beveled shaped razor edge 135 separates the prolapsed tissue 202 from the tissue mass 200. The cutting plunger is rested at a position such that its distal end is aligned with the zero mark of the tissue length indicator 103 as shown in FIG. 22 A. The tissue sample is collected into the tissue receiving port 134 of the inner cutter needle as it moves forward. During the process, the beveled shaped razor sharp knife 135 severs the prolapsed tissue sample, which then falls inside the tissue receiving port 134 on the inner cutter needle 111. The tissue sample is held in the inner cutter needle by friction with the inner walls of the inner cutter needle and by the suction created by the vacuum source, created by the pulling of the primary suction plunger and channeled through air path holes 106 and 109.

FIG. 22 A is a side view of the biopsy device after the cutting plunger is propelled by the gradient potential (or withdrawn by the suction force) toward the distal end of the cutting tube and advances into the tissue mass and slices the prolapsed tissue from the tissue mass.

FIG. 22 B illustrates a cross sectional view of the biopsy device in FIG. 22 A along the line 22A-22A where when the ridge 137 of the plunger hits the tab 203 of the stopper, it is blocked by the tab, the forward movement of the plunger is stopped and the plunger is locked in place.

The location of the ridges on the plunger determines the tissue length to be severed. Together with the cutting length indicator, this design provides a simple, accurate, precise and efficient mechanism for tissue length control.

Figure 23:
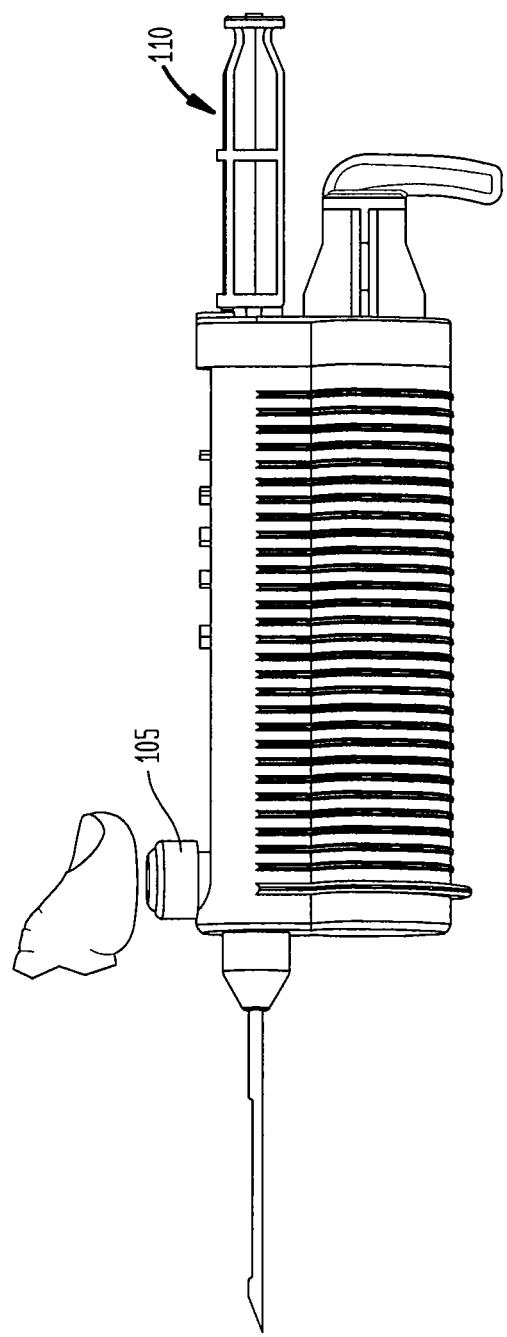
FIG. 23 shows the user removes his/her thumb from the silicone fitting to release the vacuum inside the biopsy device.

Once the tissue is severed, the silicone fitting on the air release hole is released and the air flows back to the biopsy device through air release hole 104 and air path hole 106, thus de-vacuuming the entire biopsy device as shown in FIG. 23. The suction release pathway has been discussed earlier and is shown in FIG. 10.

Figure 24:
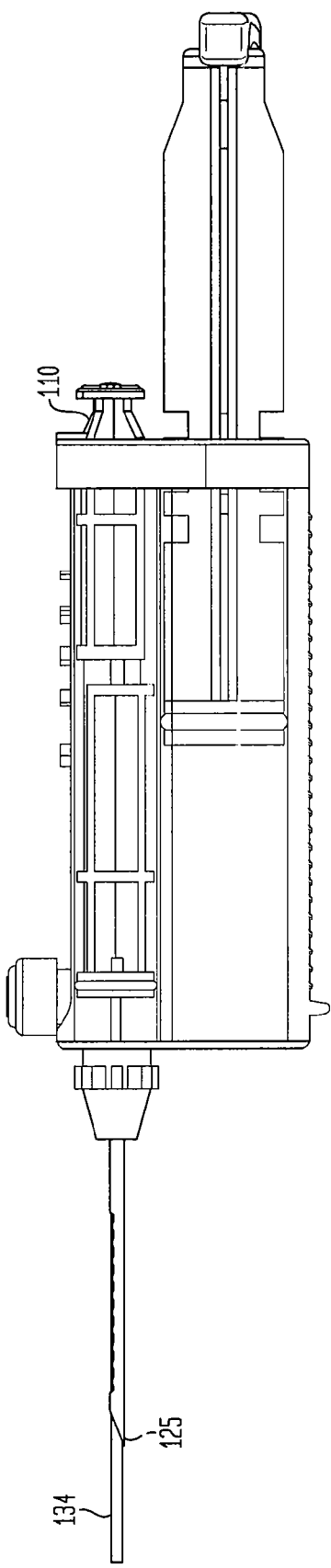
FIG. 24 shows a side view of the biopsy device being in a position to collect sample tissue.
Figure 25:
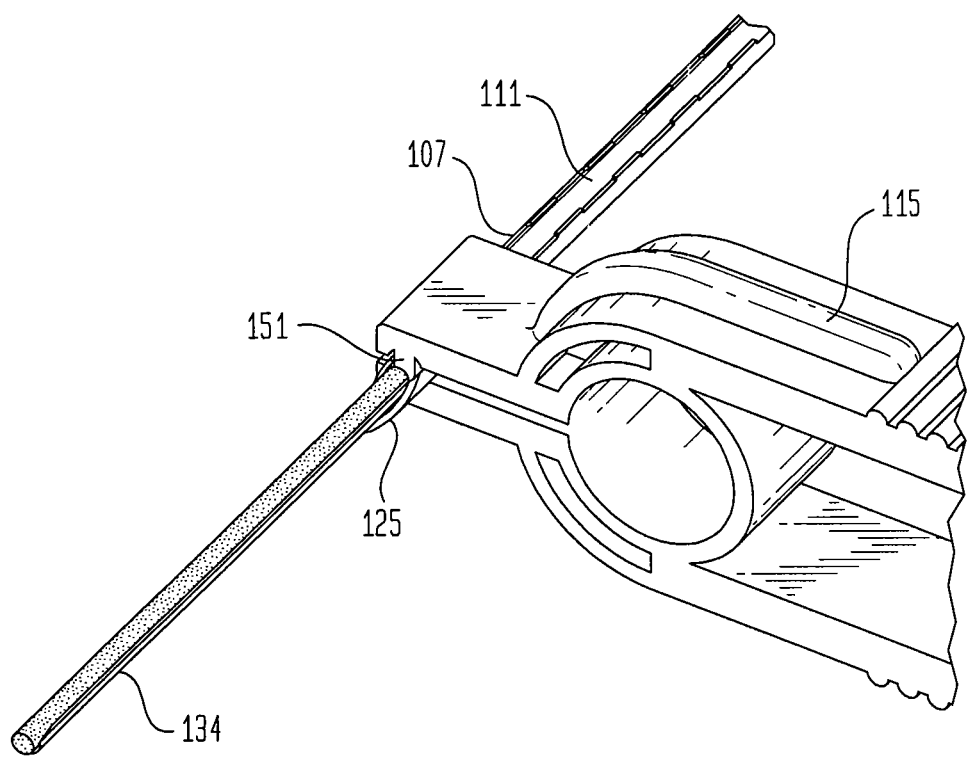
FIG. 25 illustrates a sample collector attached to the inner cutter needle at the distal end of the outer needle.

The biopsy device 10 is pulled out from the patient's body and the cutting plunger 110 is rotated until it stops. The cutting plunger is then pushed all the way in as shown in FIG. 24. At the time, the sample slot 134 of the cutting knife inner cutter needle 111 is beyond the outer needle tip 125 and the tissue sample inside is ready for collection. A sample collector 115 is then attached to the outer needle 107 near the distal end as shown in FIG. 25.

Referring to FIG. 15 there is disclosed an embodiment of the sample collector 115. The sample collector has a clip 151 on one side and a handle 153 with a compression spring 152 opposite to the clip 151. The clip 151 has a round tip of which the diameter is slightly smaller than the inner diameter of the inner cutter needle 111 so that the clip 151 can snugly fit in the tissue receiving port 134. After the user clips the sample collector 115 to the outer needle near the distal end as shown in FIG. 25, the user can pull the inner cutter needle 111 backward until the distal end of the cutting plunger 110 lines up with the mark "0" on the cutting length indicator 103. Consequently, the cylindrical sample tissue 22 is free from the device 10 and falls by gravity (FIG. 26) into a container (not shown). The sample collector 115 stays on the outer needle 107. In this way, the collected sample tissue 22 can be kept intact and undamaged for further examination. The handle 153 with the compression spring 152 is for the user to hold and operate the sample collector 115.

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

What is claimed is:

1. A disposable biopsy device comprising:
    A. a tissue cutting assembly comprising:
    an outer needle including a tissue receiving slot at a distal end of the outer needle; an elongated tube; an inner cutter needle including a tissue receiving port at a distal end of the inner cutter needle; a first plunger; and a first stopper;
    wherein
    (i) the outer needle is attached to a distal end of the tube;
    (ii) the inner cutter needle is attached to a distal end of the first plunger;
    (iii) the inner cutter needle and the first plunger are coaxially positioned within the tube and capable of rotating about and translating along the longitudinal axis of the tube;
    (iv) the inner cutter needle is coaxially positioned within the outer needle and capable of rotating about and translating along the longitudinal axis of the outer needle; and
    (v) the first stopper is attached to or connected to a proximal end of the tube; and
    B. a vacuum assembly comprising:
    an elongated cylinder; a second plunger; and a second stopper;
    wherein
    (i) the second plunger is coaxially disposed within the cylinder and capable of rotating about and translating along the longitudinal axis of the cylinder; and
    (ii) the second stopper is attached to or connected to a proximal end of the cylinder;
    wherein the vacuum assembly and the cutting assembly are two separate compartments in fluid communication through one or more air holes in between.

2. The disposable biopsy device according to claim 1, wherein the tube has one or more air path holes on a bottom surface of the tube, the cylinder has one or more air path holes on the top surface of the cylinder, and the inner cutter needle has one or more holes near its proximal end such that the vacuum generated by pulling the second plunger creates a low pressure region near the tissue receiving slot.

3. The disposable biopsy device according to claim 2, wherein the tube has an air release hole on a top surface of the tube for releasing the vacuum.

4. The disposable biopsy device according to claim 1, wherein the first plunger and the first stopper are configured to mate thereby controlling a length of tissue to be severed from a tissue mass; and the second plunger and the second stopper are configured to mate thereby controlling vacuum levels.

5. The disposable biopsy device according to claim 1, wherein the tube has a cutting length indicator which has numerical indicia corresponding to the length of tissue to be separated from the tissue mass.

6. The disposable biopsy device according to claim 1, wherein the first plunger comprises a plunger rod, one or more ridges, and one or more notches on the plunger rod, the first plunger together with the first stopper controlling the length of tissue to be severed.

7. The disposable biopsy device according to claim 1, wherein the first plunger comprises a plunger rod, a plurality of raised edges extending laterally therefrom, and a plurality of ridges disposed at predetermined position across adjacent raised edges, and a plurality of notches in front of or behind the ridges, the first plunger together with the first stopper controlling the length of tissue to be severed.

8. The disposable biopsy device according to claim 1, wherein the first plunger comprises a plunger rod, a plurality of raised edges extending laterally therefrom, and a plurality of ridges disposed at predetermined position across adjacent raised edges wherein the first stopper is configured to engage the ridge on the first plunger thereby stopping the plunger from moving forward and controlling the length of tissue.

9. The disposable biopsy device according to claim 8, wherein the first plunger has a plurality of notches thereon which allow the first plunger to be rotated, which disengages the first stopper and allows the first plunger to move further backward or forward.

10. The disposable biopsy device according to claim 1, wherein the second plunger comprises a plunger rod, and one or more ridges, and one or more notches on the plunger rod, the second plunger together with the second stopper controlling the vacuum levels.

11. The disposable biopsy device according to claim 1, wherein the second plunger and the second stopper work together to control vacuum levels, the second plunger comprising a plunger rod, a plurality of raised edges extending laterally therefrom, and a plurality of ridges disposed at predetermined position across adjacent raised edges, which when engaged, the second stopper stops the forward or backward movement of the plunger, and a plurality of notches in front of or behind the ridges, which allow the plunger to freely rotate, so that the second stopper is disengaged and the plunger is allowed to move forward or backward.

12. The disposable hand held biopsy device according to claim 1, wherein the second plunger comprises a plunger rod, a plurality of raised edges projecting laterally therefrom, and a plurality of notches breaking the raised edges, and the second stopper is configured to interlock the raised edge of the plunger and restrict the plunger from rotating freely, while the notches allow the plunger to rotate and disengage the second stopper.

13. The disposable biopsy device according to claim 1, wherein the sample receiving slot has saw teeth thereon along its lateral sides, which hold the tissue tightly prior to and at the time that the inner cutter needle advances to cut the prolapsed tissue from the tissue mass.

14. The disposable biopsy device according to claim 1, further comprising the a sample collector, which grasps the severed tissue sample out of the inner cutter needle such that the tissue sample is securely handled.

15. The disposable biopsy device according to claim 1, further comprising a shell that closely encloses the tube and cylinder.

16. The disposable biopsy device according to claim 3, further comprising a silicone fitting on top of the air release hole that seals the air release hole when pressed and releases the vacuum inside the biopsy device when released.

17. The disposable biopsy device according to claim 1, wherein the distal end of the outer needle is open and sharp such that it is easy to insert into the tissue.

18. The disposable hand held biopsy device according to claim 1, wherein the distal end of the inner cutter needle is open, beveled in shape, and contains a razor sharp edge that is effective to slice the tissue prolapsed into the tissue receiving slot and collect the severed tissue in its tissue receiving port.

19. The disposable biopsy device according to claim 1, wherein the first and second stoppers are continued as one unit or are two separate units.

20. A method of obtaining a tissue sample for biopsy examination using a disposable hand held biopsy device, the method comprising:
(a) providing a disposable biopsy device, the device comprising:
 (1) a tissue cutting assembly comprising:
  an outer needle comprising a tissue receiving slot at a distal end of the outer needle and saw teeth along lateral sides of the tissue receiving slot; an elongated tube comprising an air release hole and a cutting length indicator on a top surface of the tube; an inner cutter needle comprising a tissue receiving port at a distal end of the inner cutter needle; a first plunger; a first stopper; a silicone fitting on top of the air release hole; and a tissue sample collector;
  wherein
  (i) the outer needle is attached to a distal end of the tube;
  (ii) the inner cutter needle is attached to a distal end of the first plunger;
  (iii) the inner cutter needle and the first plunger are coaxially positioned within the tube and capable of rotating about and translating along the longitudinal axis of the tube;
  (iv) the inner cutter needle is coaxially positioned within the outer needle and capable of rotating about and translating along the longitudinal axis of the outer needle; and
  (v) the first stopper is attached to or connected to a proximal end of the tube; and
 (2) a vacuum assembly comprising:
  an elongated cylinder; a second plunger; and a second stopper;
  wherein
  (i) the second plunger is coaxially disposed within the cylinder and capable of rotating about and translating along the longitudinal axis of the cylinder; and
  (ii) the second stopper is attached to or connected to a proximal end of the cylinder;
 wherein the vacuum assembly and the cutting assembly are two separate compartments in fluid communication through one or more air holes in between; and
(b) placing the outer needle at a location of collecting sample tissue;
(c) covering the air release hole;
(d) withdrawing the second plunger, rotating the plunger, and locking the plunger in place;
(e) pulling the first plunger backward such that its distal end is aligned with one of the numerical indicia on the cutting length indicator corresponding to a desired tissue length, exposing the tissue receiving slot on the outer needle so that the tissue prolapses into the sample receiving slot and is held tight by the vacuum and the saw teeth along the tissue receiving slot;
(f) releasing the first plunger and the attached inner cutter needle, which are then propelled by a gradient pressure to advance into the tissue receiving slot and sever the tissue, which has prolapsed into the sample port, and stops when it hits the first stopper;
(g) allowing air flow into the biopsy device, releasing the vacuum;
(h) pulling the biopsy device out from the body; and once outside the body,
 (1) turning the first plunger clockwise until it stops;

(2) pushing the first plunger all the way forwards;
(3) grasping the outer needle near the distal end of the outer needle using the sample collector; and
(4) pulling the inner cutter needle backward to allow the severed tissue sample to fall out of the device by gravity.

21. The method according to claim 20, wherein the tube has one or more air path holes on the bottom surface, the cylinder has one or more air path holes on the top surface and the inner cutter needle has one or more holes near its proximal end, such that the vacuum generated by pulling the second plunger creates the low pressure region near the tissue receiving slot.

22. The method according to claim 20, wherein the first plunger and the first stopper are configured to mate thereby controlling the length of the tissue to be severed from the tissue mass; and the second plunger and the second stopper are configured to mate thereby controlling the vacuum levels.

23. The method according to claim 20, wherein the first plunger comprises a plunger rod, one or more ridges, and one or more notches on the plunger rod, the first plunger together with the first stopper controlling the length of tissue to be severed.

24. The method according to claim 20, wherein the first plunger comprises a plunger rod, a plurality of raised edges extending laterally therefrom, a plurality of ridges disposed at predetermined position across adjacent raised edges, and a plurality of notches in front of or behind the ridges, the first plunger together with the first stopper controlling the length of tissue to be severed.

25. The method according to claim 20, wherein the first plunger comprises a plunger rod, a plurality of raised edges extending laterally therefrom, a plurality of ridges disposed at a predetermined position across adjacent raised edges, wherein the first stopper is configured to engage the ridge on the first plunger thereby stopping the plunger from moving forward whereby controlling the tissue length and a plurality notches thereon, which allow the first plunger to be rotated, thereby dis-engaging the first stopper and allowing the first plunger to move further backward or forward.

26. The method according to claim 20, wherein the second plunger comprises a plunger rod, one or more ridges, and one or more notches on the plunger rod, the second plunger together with the second stopper controlling the vacuum levels.

27. The method according to claim 20, wherein the second plunger and the second stopper work together to control the vacuum levels, the second plunger comprising a plunger rod, a plurality of raised edges extending laterally therefrom, and a plurality of ridges disposed at predetermined positions across adjacent raised edges, which when they engage the second stopper stops the forward or backward movement of the plunger, and a plurality of notches in front of or behind the ridges, which allow the plunger to freely rotate thereby disengaging the second stopper and allowing the plunger to move forward or backward.

28. The method according to claim 20, wherein the second plunger comprises a plunger rod, and a plurality of raised edges projecting laterally therefrom, wherein the second stopper is configured to interlock the raised edge of the plunger, restricting the plunger from rotating freely, and the plunger has a plurality of notches allowing the plunger to rotate and disengage the second stopper.

29. The method according to claim 20, wherein the disposable biopsy device further comprising a shell that closely encloses the tube and cylinder.

30. The method according to claim 20, wherein the distal end of the outer needle is open and sharp such that it is easy to insert into the tissue and the distal end of the inner cutter needle is open, beveled in shape, and contains a razor sharp edge, the distal end of the inner cutter needle slicing the tissue prolapsed into the tissue receiving slot and collecting the severed tissue in its tissue receiving port.

\* \* \* \* \*